US012167885B2

(12) United States Patent
Smith

(10) Patent No.: US 12,167,885 B2
(45) Date of Patent: Dec. 17, 2024

(54) ELECTROSURGICAL ENERGY ADAPTER, ELECTROSURGICAL ENERGY CONTROL, AND SURGICAL MULTI-TOOL

(71) Applicant: Divyze, Inc., Wellington, NV (US)

(72) Inventor: Ryan D. Smith, Wellington, NV (US)

(73) Assignee: Divyze, Inc., Wellington, NV (US)

( * ) Notice: Subject to any disclaimer, the term of this patent is extended or adjusted under 35 U.S.C. 154(b) by 0 days.

(21) Appl. No.: 17/670,831

(22) Filed: Feb. 14, 2022

(65) Prior Publication Data

US 2022/0160416 A1    May 26, 2022

Related U.S. Application Data

(63) Continuation of application No. PCT/US2020/046156, filed on Aug. 13, 2020.
(Continued)

(51) Int. Cl.
*A61B 18/12*    (2006.01)
*A61B 18/00*    (2006.01)
*A61B 18/14*    (2006.01)

(52) U.S. Cl.
CPC ...... *A61B 18/1206* (2013.01); *A61B 18/1442* (2013.01); *A61B 2018/00172* (2013.01);
(Continued)

(58) Field of Classification Search
CPC ............ A61B 18/1206; A61B 18/1442; A61B 2018/00172; A61B 2018/00607;
(Continued)

(56) References Cited

U.S. PATENT DOCUMENTS

| 462,270 A | 11/1891 | McConnaughey |
| 2,895,478 A | 7/1959 | Post |

(Continued)

FOREIGN PATENT DOCUMENTS

| JP | 10-000199 | 1/1998 |
| JP | H10 24177 | 1/1998 |

(Continued)

OTHER PUBLICATIONS

Surgical Neurology International, 2012, vol. 3, No. 152, pp. 1-3, published Dec. 14, 2012.
(Continued)

*Primary Examiner* — Michael F Peffley
*Assistant Examiner* — Samantha M Good
(74) *Attorney, Agent, or Firm* — Knobbe, Martens, Olson & Bear, LLP

(57) ABSTRACT

An electrosurgical system including an electrosurgical generator and an adapter connected to the electrosurgical generator. The adapter is configured to selectively transmit one or more energy outputs from the electrosurgical generator to an end effect device. At least one of the electrosurgical generator and the adapter are configured to be controlled by one or more control device. An electrosurgical system can include a control device connected to an electrosurgical generator. The control device can be configured to selectively transmit control instructions to the electrosurgical generator. The control device can be configured to receive a control signal from a user. An electrosurgical apparatus can include a pair of blades configured to deliver at least mechanical and electrical energy to tissue. Each blade can include a portion configured to protrude to the other side of a central plane. An electrosurgical apparatus can include a first tip comprising a first tip central plane and a second tip comprising a second tip central plane, wherein the electro-
(Continued)

surgical apparatus has a first configuration wherein the first and second tips operate as forceps, and wherein the electrosurgical apparatus has a second configuration wherein the first and second tips operate as scissors. The electrosurgical apparatus can have restricted movement in the forceps configuration and limited shearing movement in the scissors configuration.

21 Claims, 18 Drawing Sheets

Related U.S. Application Data

(60) Provisional application No. 62/887,919, filed on Aug. 16, 2019, provisional application No. 62/887,980, filed on Aug. 16, 2019, provisional application No. 62/887,943, filed on Aug. 16, 2019.

(52) U.S. Cl.
CPC .......... *A61B 2018/00607* (2013.01); *A61B 2018/00767* (2013.01); *A61B 2018/00958* (2013.01); *A61B 2018/00994* (2013.01); *A61B 2018/1253* (2013.01); *A61B 2018/126* (2013.01)

(58) Field of Classification Search
CPC .......... A61B 2018/00767; A61B 2018/00958; A61B 2018/00994; A61B 2018/1253; A61B 2018/126

See application file for complete search history.

(56) References Cited

U.S. PATENT DOCUMENTS

| | | | |
|---|---|---|---|
| 3,651,811 A | 3/1972 | Hildebrandt et al. | |
| 3,977,410 A | 8/1976 | Huston et al. | |
| 4,478,221 A | 10/1984 | Heiss | |
| 4,669,470 A | 6/1987 | Brandfield | |
| 4,819,636 A | 4/1989 | Gerich et al. | |
| 5,047,049 A | 9/1991 | Salai | |
| 5,637,111 A | 6/1997 | Sutcu | |
| 5,964,756 A | 10/1999 | McGaffigan et al. | |
| 5,976,129 A * | 11/1999 | Desai ................ | A61B 18/1477 606/42 |
| 6,096,059 A | 8/2000 | Kuzma | |
| 6,106,542 A | 8/2000 | Toybin et al. | |
| 6,113,596 A | 9/2000 | Hooven et al. | |
| 6,283,963 B1 | 9/2001 | Regula | |
| 6,391,043 B1 | 5/2002 | Moll et al. | |
| 6,458,129 B2 | 10/2002 | Scarfi | |
| 6,592,603 B2 | 7/2003 | Lasner | |
| 6,773,434 B2 | 8/2004 | Ciarrocca | |
| 6,976,992 B2 | 12/2005 | Sachatello et al. | |
| 7,208,005 B2 | 4/2007 | Frecker et al. | |
| 7,410,494 B2 | 8/2008 | Kalmann et al. | |
| 7,544,195 B2 | 6/2009 | Lunsford et al. | |
| 8,114,074 B1 | 2/2012 | Slater | |
| 8,398,673 B2 | 3/2013 | Hinchliffe et al. | |
| 8,597,293 B2 | 12/2013 | Falkenstein et al. | |
| RE44,834 E * | 4/2014 | Dumbauld ....... | A61B 17/32056 606/45 |
| 9,050,101 B1 | 6/2015 | Smith | |
| 9,393,066 B2 | 7/2016 | Smith | |
| 9,931,155 B2 | 4/2018 | Smith | |
| 9,943,327 B2 | 4/2018 | Smith | |
| 10,792,065 B2 | 10/2020 | Smith | |
| 11,020,168 B2 | 6/2021 | Smith | |
| 2003/0065358 A1 | 4/2003 | Frecker et al. | |
| 2003/0073987 A1 | 4/2003 | Sakurai et al. | |
| 2003/0073991 A1 | 4/2003 | Francischelli | |
| 2004/0153061 A1 | 8/2004 | Wang | |
| 2006/0167450 A1 | 7/2006 | Johnson et al. | |
| 2007/0118111 A1 | 5/2007 | Weinberg | |
| 2007/0244515 A1 | 10/2007 | Fanous | |
| 2010/0023001 A1 | 1/2010 | Hosaka et al. | |
| 2010/0274244 A1 | 10/2010 | Heard | |
| 2011/0238066 A1 | 9/2011 | Olson | |
| 2012/0083827 A1 | 4/2012 | Artale | |
| 2012/0209305 A1 | 8/2012 | Deodhar et al. | |
| 2013/0138101 A1 * | 5/2013 | Kerr .................... | A61B 18/1442 606/45 |
| 2013/0178852 A1 * | 7/2013 | Allen, IV ........... | A61B 18/1447 606/41 |
| 2013/0253499 A1 | 9/2013 | Kimball et al. | |
| 2015/0141992 A1 | 5/2015 | Smith | |
| 2015/0209099 A1 | 7/2015 | Atwell et al. | |
| 2015/0313667 A1 | 11/2015 | Allen | |
| 2015/0327911 A1 | 11/2015 | Smith | |
| 2016/0113731 A1 | 4/2016 | Stokes et al. | |
| 2017/0128125 A1 | 5/2017 | Smith | |
| 2019/0076181 A1 | 4/2019 | Smith | |
| 2019/0083120 A1 | 4/2019 | Smith | |

FOREIGN PATENT DOCUMENTS

| | | |
|---|---|---|
| JP | 2001037769 | 2/2001 |
| JP | 2008-100350 | 5/2008 |
| WO | WO 01/66025 | 9/2001 |
| WO | WO 2015/077350 | 5/2015 |
| WO | WO 2017/203231 | 11/2017 |

OTHER PUBLICATIONS

Written Opinion of the International Searching Authority for PCT/US2014/066432, mailed Mar. 13, 2015 in 6 pages.
European Search Report for EP Application No. 14864016.2, mailed Jul. 20, 2017.
Matsumura. Nobuhisa, A new bayonet spring microsurgical instrument handle 1-21 with a bar for microneurosurgery, Surgical Neurology International, 2012. vol. 3, No. 152, pp. 1-3 (internal).
Written Opinion of the International Searching Authority for PCT/US2017/038381, mailed Sep. 19, 2017 in 13 pages.
Japanese Office Action for JP Application No. 2016-533089, mailed Jul. 31, 2018.
First Examination Report for AU Application No. 2014353067, mailed Aug. 3, 2018.
Japanese Office Action for JP Application No. 2016-533089, mailed May 21, 2019.
Notice of Acceptance for AU Application No. 2014353067, mailed Jul. 4, 2019.
Japanese Office Action for JP Application No. 2016-533089, mailed Dec. 3, 2019.
Indian Office Action for IN Application No. 201617020197, mailed Jan. 30, 2020.
Written Opinion of the International Searching Authority for PCT/US2020/046156, mailed Jan. 25, 2021 in 14 pages.
Canadian Office Action for CA Application No. 2930605, mailed Sep. 15, 2022.
European Search Report for EP Application No. 20854288.6, mailed Jul. 11, 2023.

* cited by examiner

ELECTROSURGICAL ENERGY ADAPTER, ELECTROSURGICAL ENERGY CONTROL, AND SURGICAL MULTI-TOOL

INCORPORATION BY REFERENCE TO ANY PRIORITY APPLICATIONS

The present application is a continuation of International Application No. PCT/US2020/046156, filed Aug. 13, 2020, which claims priority benefit under 35 U.S.C. § 119(e) of U.S. Provisional Patent Application No. 62/887,980 filed Aug. 16, 2019, U.S. Provisional Patent Application No. 62/887,943 filed Aug. 16, 2019, and U.S. Provisional Patent Application No. 62/887,919 filed Aug. 16, 2019, the disclosures of each are incorporated by reference herein in their entirety. Further details regarding apparatuses and methods that may be utilized or incorporated with the embodiments described herein are found in U.S. Pat. No. 9,050,101 issued Jun. 9, 2015 and U.S. Pat. No. 9,943,327 issued Apr. 17, 2018, the entireties of each of which are hereby incorporated by reference.

BACKGROUND

Field of the Invention

The present application relates to the field of medical devices, and encompasses apparatuses for use during surgery and surgical methods. In particular, the application relates to electrosurgical energy adapters, electrosurgical energy control, surgical multitools, and methods of use.

SUMMARY

Surgeons often use mechanical, electrosurgical, and ultrasonic techniques in varying amounts to physically help a patient. Procedures are inherently risky and eliminating steps and combining the devices used will reduce costs and complications and allow for more patients to be helped.

Electrosurgical generators transform readily available electrical energy (i.e. from a wall outlet) into energy usable in electrosurgery with the energy varying in frequency, voltage, current, duty cycle, etc. This transformed energy is then transmitted to tissue through any of number of devices. Transmission of the energy from the generator to the tissue is controlled by any number of control devices.

The electrosurgical generator performs the critical role of transforming the energy to forms required by electrosurgery, with some forms being preferred for certain functions and procedures. Any form produced by a generator must be efficiently transmitted to the tissue to be acted on and numerous devices perform this function. Different forms or modes are typically transmitted to tissue through unique and separate devices. Devices that can deliver multiple energy modalities are advantageous to achieve the optimal tissue effect and expedite procedures.

Electrosurgical energy controlling or activating devices are often connected through physical wire(s) to the energy generating or transforming unit. Wired devices are bulky in nature and are limited to the specific number of physical connection inputs. Wire devices are placed on the surgical floor in a position relative to the surgeon or user. The control device must be repositioned, or the user adjust their posture and stance, to optimize the approach to the surgical site and simultaneously operate the electrosurgery control device.

It is an object of this disclosure to demonstrate a means of controlling an electrosurgical system with a device continuously integrated with a user or surgeon's command, without regard to their position relative to the patient or surgical conditions.

End-effect devices that combine energy effects are well known to the field and can include "cut" and "coagulation" functions for "monopolar" energy (one dispersive electrode is distant from the active, tissue effecting electrode), and mechanical shearing and coagulation through "bipolar" energy (two tissue effecting electrodes in proximity).

It is an object of this disclosure to demonstrate a means of transmitting multiple forms of tissue effecting energy to a single end-effect device.

Devices able to deliver multiple forms of energy, including mechanical, electrical, etc., are well known to the field and may include devices for laparoscopic or open surgery. Devices that can perform multiple functions are advantageous to reduce the size of the device and therefore the incision or wound required for access, amongst other reasons.

Tissue contacting end effect components are often designed to deliver one form of energy, for example mechanical shearing. Other components are designed to deliver other forms of energy, for example electrical. Tissue contacting and energy transmitting components are well known to delivery multiple types of energy.

It is an object of this disclosure to demonstrate a design to facilitate further modes interaction for efficiently delivering energy to tissue by various modes.

In some embodiments, a system is provided. The system can include an end effect device. The system can include an electrosurgical generator. The system can include an adapter. In some embodiments, the adapter is configured to selectively transmit one or more energy outputs from the electrosurgical generator to the end effect device. The system can include a control device.

In some embodiments, at least one of the electrosurgical generator and the adapter are configured to be controlled by the control device. In some embodiments, at least one of the electrosurgical generator and the adapter is configured to be selectively activated by the control device. In some embodiments, the end effect device is configured to transmit energy. In some embodiments, the adapter is configured to control the form of energy transmitted by the end effect device. In some embodiments, the adapter is configured to transmit, combine, or transform any form or forms of control input into one or more different forms of control inputs. In some embodiments, the control device is configured to selectively transmit control instructions to the electrosurgical generator. In some embodiments, the control device is configured to receive a control signal from a user. In some embodiments, a user control transmits one or more signals to the control device. In some embodiments, a user control transmits wirelessly. In some embodiments, a user control comprises one or more sensors. In some embodiments, one or more sensors are configured to detect movement. In some embodiments, one or more sensors are configured to detect pressure, proximity, sound, voice command, etc. In some embodiments, the one or more sensors are configured to detect the user's intention. In some embodiments, a switch is configured to be activated only while a sensor is in a particular range. In some embodiments, a switch is configured to be activated only while a sensor is in a particular range of distance, capacitance, etc. In some embodiments, a user control transmits output instructions to the control device. In some embodiments, a user control comprises one or more sensors coupled with a garment. In some embodiments, the end effect device comprises a pair of blades configured to deliver at least mechanical and electrical energy to tissue. In some embodiments, each blade comprises a portion configured to protrude to the other side of a central plane. In some embodiments, the pair of blades is configured to be moved to the central plane such that movement away from the central plane is selectively restricted. In some embodiments, the pair of blades is configured to be moved to the central plane such that movement cross the central plane is selectively restricted. In some embodiments, the pair of blades is configured to be moved to the central plane such that movement away from and/or across the central plane is selectively restricted. In some embodiments, the pair of blades is configured such that opposing movement along the same central plane produces interference between the pair of blades. In some embodiments, the end effect device is configured to conduct electricity.

In some embodiments, an electrosurgical apparatus is provided. The electrosurgical apparatus can include a pair of blades configured to deliver at least mechanical and electrical energy to tissue. In some embodiments, each blade comprises a portion configured to protrude to the other side of a central plane. In some embodiments, the pair of blades is configured to be moved to the central plane such that movement away from and/or across the central plane is selectively restricted.

In some embodiments, the pair of blades is configured to be moved to the central plane such that movement away from and/or across the central plane is simultaneously restricted. In some embodiments, the pair of blades is configured to directly deliver at least mechanical and electrical energy to tissue. In some embodiments, the pair of blades comprise one or more surfaces compatible with transmission of electrosurgical energy. In some embodiments, the pair of blades comprise one or more surfaces compatible with transmission of pinching mechanical energy. In some embodiments, the pair of blades comprise one or more surfaces compatible with transmission of shearing mechanical energy. In some embodiments, the pair of blades is configured such that opposing movement along the same central plane produces interference between the pair of blades.

In some embodiments, an electrosurgical system is provided. The electrosurgical system can include an adapter connected to an electrosurgical generator. In some embodiments, the adapter is configured to selectively transmit one or more energy outputs from the electrosurgical generator to an end effect device. In some embodiments, at least one of the electrosurgical generator and the adapter are configured to be controlled by one or more control device. In some embodiments, the adapter can transmit one or multiple forms of energy to the end effect device, while protecting the generator from receiving this energy inappropriately (i.e. to a different output circuit).

In some embodiments, the electrosurgical system can include the electrosurgical generator. In some embodiments, the electrosurgical system can include the control device. In some embodiments, the electrosurgical system can include the end effect device. In some embodiments, the electrosurgical generator and the adapter are separate components. In some embodiments, the electrosurgical generator and the adapter are integrated components. In some embodiments, the electrosurgical generator and the adapter are integrated with an energy source. In some embodiments, the electrosurgical generator and the adapter are integrated with the control device. In some embodiments, at least one of the electrosurgical generator and the adapter is configured to be selectively activated by a control input. In some embodiments, at least one of the electrosurgical generator and the adapter is configured to be selectively activated by one or more control inputs. In some embodiments, the adapter is configured to selectively transmit one or more energy outputs from the electrosurgical generator to one or more end effect devices. In some embodiments, the end effect device is configured to transmit energy. In some embodiments, the adapter is configured to control the form of energy transmitted by the end effect device. In some embodiments, the adapter is configured to receive one type of energy and transmit a different type of energy. In some embodiments, the adapter is configured to receive one type of energy and transmit the same type of energy. In some embodiments, the adapter is configured to receive a plurality of types of energy and transmit one type of energy. In some embodiments, the adapter is configured to receive a plurality of types of energy and transmit a plurality of types of energy. In some embodiments, the adapter is configured to receive one type of energy from the electrosurgical generator and transmit a plurality of types of energy. In some embodiments, the adapter is configured to transmit, combine, or transform any form or forms of energy into one or more different forms of energy. In some embodiments, the adapter is configured to select which types of energy are transmitted. In some embodiments, the adapter is configured to select which type or types of energy are transmitted. In some embodiments, the adapter is configured to select which types of energy are transmitted by one or more control inputs. In some embodiments, the control input comprises a sensor, switch, algorithms, or a combination of a sensor, switch, or algorithm. In some embodiments, the adapter is configured to selectively transmit one or more control input from one or more control device to the electrosurgical generator. In some embodiments, the adapter can receive control input from a control device, the generator or end-effect device. In some embodiments, the adapter can detect the state of one or multiple components and allowing or disallowing energy transmission based on one or a multitude of inputs. In some embodiments, the control device is configured to transmit a control input. In some embodiments, the adapter is configured to control the form of control input transmitted to the electrosurgical generator. In some embodiments, the adapter is configured to receive one type of control input and transmit a different type of control input. In some embodiments, the adapter is configured to receive one type of control input and transmit a different type of control input such as wireless in and wired out. In some embodiments, the adapter is configured to receive one type of control input and transmit a different type of control input, such as any signal the devices can correctly interpret. In some embodiments, the adapter is configured to receive one type of control input and transmit the same type of control input. In some embodiments, the adapter is configured to receive a plurality of control inputs and transmit one type of control input. In some embodiments, the adapter is configured to receive a plurality of control inputs and transmit a plurality of control inputs. In some embodiments, the adapter is configured to receive one type of control input from the electrosurgical generator and transmit a plurality of types of control inputs. In some embodiments, the adapter is configured to transmit, combine, or transform any form or forms of control input into one or more different forms of control inputs. In some embodiments, the adapter is configured to select which control inputs are transmitted. In some embodiments, the adapter is configured to prevent energy output of one form being transmitted to another output circuit that is not being used. In some embodiments, the adapter is configured to prevent energy output being transmitted to an output circuit that can be damaged. In some embodiments, the adapter is configured to selectively transmit one or more energy outputs from one or more end effect devices to one or more electrosurgical generators. In some embodiments, the adapter is configured to selectively transmit one or more energy outputs back to the electrosurgical generator. In some embodiments, the adapter is configured to selectively transmit one or more energy outputs. In some embodiments, the adapter can transmit one or multiple forms of energy to the end effect device, while the adapter can protect the generator from receiving this energy inappropriately, such as to a different output circuit.

In some embodiments, an electrosurgical system is provided. The electrosurgical system can include a control device connected to an electrosurgical generator. In some embodiments, the control device is configured to selectively transmit control instructions to the electrosurgical generator. In some embodiments, the control device is configured to receive a control signal from a user. In some embodiments, the control device is configured to receive a control signal from an operator. In some embodiments, the control device is configured to receive a control signal from another device.

In some embodiments, a user control is coupled to the user. In some embodiments, a user control transmits one or more signals to the control device. In some embodiments, a user control transmits wirelessly. In some embodiments, a user control transmits through a wired connection. In some embodiments, a user control comprises one or more sensors. In some embodiments, the sensors can be configured to receive any type of signal (electrical, pressure, sound, position, etc.) In some embodiments, a user control comprises one or more switches. In some embodiments, a user control comprises one or more algorithms. In some embodiments, a user control transmits through a dedicated connection. In some embodiments, a user control transmits through numerous connections. In some embodiments, a user control transmits a signal. In some embodiments, a user control transmits output instructions to the control device. In some embodiments, a user control comprises one or more user inputs. In some embodiments, a user control comprises one or more sensors coupled with a garment. In some embodiments, a user control comprises one or more sensors coupled with a sock. In some embodiments, a user control comprises one or more sensors coupled with a glove. In some embodiments, a user control comprises one or more sensors coupled with a shoe. In some embodiments, a user control comprises one or more sensors coupled with an insole. In some embodiments, any sensor can be directly coupled to biological signals (muscle, nerve, etc.) In some embodiments, sensor data is configured to be transmitted wirelessly to a switch. In some embodiments, a signal from a sensor of a user control is configured to be processed before transmission. In some embodiments, a signal from a sensor of a user control is configured to be processed after transmission. In some embodiments, one or more sensors are configured to be activated simultaneously. In some embodiments, one or more sensors are configured to detect movement. In some embodiments, one or more sensors are configured to output a plurality of signals. In some embodiments, one or more sensors are configured to output one or more readings. In some embodiments, a combination of readings within a range is configured to produce a particular output. In some embodiments, a second combination of readings within a range is configured to produce a second different output. In some embodiments, a plurality of readings, each within a range, is configured to each produce a distinct output. In some embodiments, a continuous reading is configured to produce a continuous output. In some embodiments, a continuous reading through time is configured to produce a continuous output. In some embodiments, a continuous reading through relative pressure is configured to produce a continuous output. In some embodiments, a continuous reading through positional differences is configured to produce a continuous output. In some embodiments, a wireless transmitter is configured to be permanently paired with a user control. In some embodiments, a wireless transmitter is configured to be paired by user input. In some embodiments, a switch is configured to be activated only while a sensor is in a particular range. In some embodiments, a switch is configured to be activated only while a sensor is in a particular range, such as proximity or other. In some embodiments, a switch is configured to be activated in any range of distance. In some embodiments, the system includes a wired connection. In some embodiments, an end effect device is configured to function as the control device. In some embodiments, an end effect device is configured to transmit to an adapter its particular mechanical, electrical, or position status. In some embodiments, an end effect device is configured to transmit to an generator its particular mechanical, electrical, or position status.

In some embodiments, an electrosurgical apparatus is provided. The electrosurgical apparatus can include a pair of blades configured to deliver at least mechanical and electrical energy to tissue. In some embodiments, each blade comprises a portion configured to protrude to the other side of a central plane.

In some embodiments, the pair of blades is configured to directly deliver at least mechanical and electrical energy to tissue. In some embodiments, the pair of blades is configured such that movement toward and away from the central plane is selectively restricted. In some embodiments, the pair of blades is configured to be moved to the central plane such that movement away from the central plane is selectively restricted. In some embodiments, the pair of blades is configured such that opposing movement along the same central plane produces interference between the pair of blades. In some embodiments, the pair of blades comprise one or more surfaces compatible with transmission of electrosurgical energy. In some embodiments, the pair of blades comprise one or more surfaces compatible with transmission of pinching mechanical energy. In some embodiments, the pair of blades comprise one or more surfaces compatible with transmission of shearing mechanical energy.

In some embodiments, an electrosurgical apparatus is provided. The electrosurgical apparatus can include a first tip comprising a first tip central plane. The electrosurgical apparatus can include a second tip comprising a second tip central plane. In some embodiments, the electrosurgical apparatus has a first configuration wherein the first and second tips operate as forceps or a probe. In some embodiments, the electrosurgical apparatus has a second configuration wherein the first and second tips operate as scissors. In some embodiments, the electrosurgical apparatus is configured to have restricted movement in the forceps or probe configuration and limited shearing movement in the scissors configuration.

In some embodiments, the first and second tips operate as bipolar forceps in the first configuration. In some embodiments, the surgical tool is configured to transmit or conduct electricity. In some embodiments, the electrosurgical apparatus can include a mechanism configured to cause the shearing of the first tip and the second tip. In some embodiments, the first tip or the second tip is configured to conduct electrical energy. In some embodiments, the first tip and the second tip are configured to conduct electrical energy. In some embodiments, a protrusion of the first tip and a protrusion of the second tip are configured to retain the first tip and the second tip in proximity to each other. In some embodiments, a protrusion of the first tip and a protrusion of the second tip are configured to selectively limit movement of at least one of the first tip and the second tip. In some embodiments, a protrusion of the first tip and a protrusion of the second tip are configured to selectively couple the first tip and the second tip. In some embodiments, a protrusion of the first tip and a protrusion of the second tip are configured to selectively allow movement of at least one of the first tip and the second tip in at least one direction. In some embodiments, a protrusion of the first tip and a protrusion of the second tip are configured to selectively restrict movement of at least one of the first tip and the second tip in at least one direction.

In some embodiments, a method of using a surgical tool is provided. The method can include providing a first tip and a second tip coupled to each other, the first tip comprising a first tip central plane, the second tip comprising a second tip central plane, wherein the first and second tips are configured for use as forceps or a probe in a first configuration. The method can include reconfiguring the first and second tips, such that after reconfiguration, the first and second tips are configured for use as scissors in a second configuration, wherein the surgical tool is configured to transition between the first configuration and the second configuration, at least in part, by separating the blades and reestablishing a scissor axis by rotating the first tip and the second tip. In some embodiments, the surgical tool can be configured to a third configuration where the first and second tips are approximated. The tool can operate as a probe in the third configuration. In some embodiments, the tool can selectively transmit mechanical or electrical energy in the third configuration. In some embodiments, the tool can selectively transmit one or multiple types of energy in any configuration. In some embodiments, the tool can act as a sensor, detecting conditions of tissue and transmitting information to a user or other device.

In some embodiments, the method can include conducting electrical current to an electrode in the first tip or the second tip. In some embodiments, the method can include conducting electrical current to the electrode when the first and second tips are configured for use as forceps. In some embodiments, the method can include applying electrical energy with the first tip or the second tip. In some embodiments, the method can include bringing the first and second tips into proximity or contact with each other in the forceps configuration. In some embodiments, the method can include interlocking the first and second tips in the forceps configuration.

In some embodiments, an electrosurgical apparatus is provided. The electrosurgical apparatus can include a first tip comprising a first tip central plane. The electrosurgical apparatus can include a second tip comprising a second tip central plane. In some embodiments, the electrosurgical apparatus has a first configuration wherein the first and second tips operate as forceps. In some embodiments, the electrosurgical apparatus has a second configuration wherein the first and second tips operate as scissors. In some embodiments, the electrosurgical apparatus has a third configuration wherein the first and second tips operate as a probe. In some embodiments, the electrosurgical apparatus is configured to have restricted movement in the forceps configuration and limited shearing movement in the scissors configuration.

In some embodiments, the first and second tips operate as bipolar forceps in the first configuration. In some embodiments, the surgical tool is configured to transmit or conduct electricity. In some embodiments, the electrosurgical apparatus can include a mechanism configured to cause the shearing of the first tip and the second tip. In some embodiments, the first tip or the second tip is configured to conduct electrical energy. In some embodiments, the first tip and the second tip are configured to conduct electrical energy. In some embodiments, a protrusion of the first tip and a protrusion of the second tip are configured to retain the first tip and the second tip in proximity to each other. In some embodiments, a protrusion of the first tip and a protrusion of the second tip are configured to selectively limit movement of at least one of the first tip and the second tip. In some embodiments, a protrusion of the first tip and a protrusion of the second tip are configured to selectively couple the first tip and the second tip. In some embodiments, a protrusion of the first tip and a protrusion of the second tip are configured to selectively allow movement of at least one of the first tip and the second tip in at least one direction. In some embodiments, a protrusion of the first tip and a protrusion of the second tip are configured to selectively restrict movement of at least one of the first tip and the second tip in at least one direction.

In some embodiments, a method of using a surgical tool is provided. The method can include providing a first tip and a second tip coupled to each other. In some embodiments, the first tip comprises a first tip central plane. In some embodiments, the second tip comprises a second tip central plane. In some embodiments, the first and second tips are configured for use as forceps in a first configuration. The method can include reconfiguring the first and second tips, such that after reconfiguration, the first and second tips are configured for use as scissors in a second configuration. In some embodiments, the surgical tool is configured to transition between the first configuration and the second configuration, at least in part, by separating the blades and reestablishing a scissor axis by rotating the first tip and the second tip. The method can include reconfiguring the tips to use as a probe in a third configuration.

In some embodiments, the method can include conducting electrical current to an electrode in the first tip or the second tip. In some embodiments, the method can include conducting electrical current to the electrode when the first and second tips are configured for use as forceps. In some embodiments, the method can include applying electrical energy with the first tip or the second tip. In some embodiments, the method can include bringing the first and second tips into proximity or contact with each other in the forceps configuration. In some embodiments, the method can include interlocking the first and second tips in the forceps configuration.

BRIEF DESCRIPTION OF THE DRAWINGS

These and other features, aspects, and advantages of the invention disclosed herein are described below with reference to the drawings of preferred embodiments, which are intended to illustrate and not to limit the invention. Additionally, from figure to figure, the same reference numerals have been used to designate the same components of an illustrated embodiment. The following is a brief description of each of the drawings.

DETAILED DESCRIPTION

Figure 1:
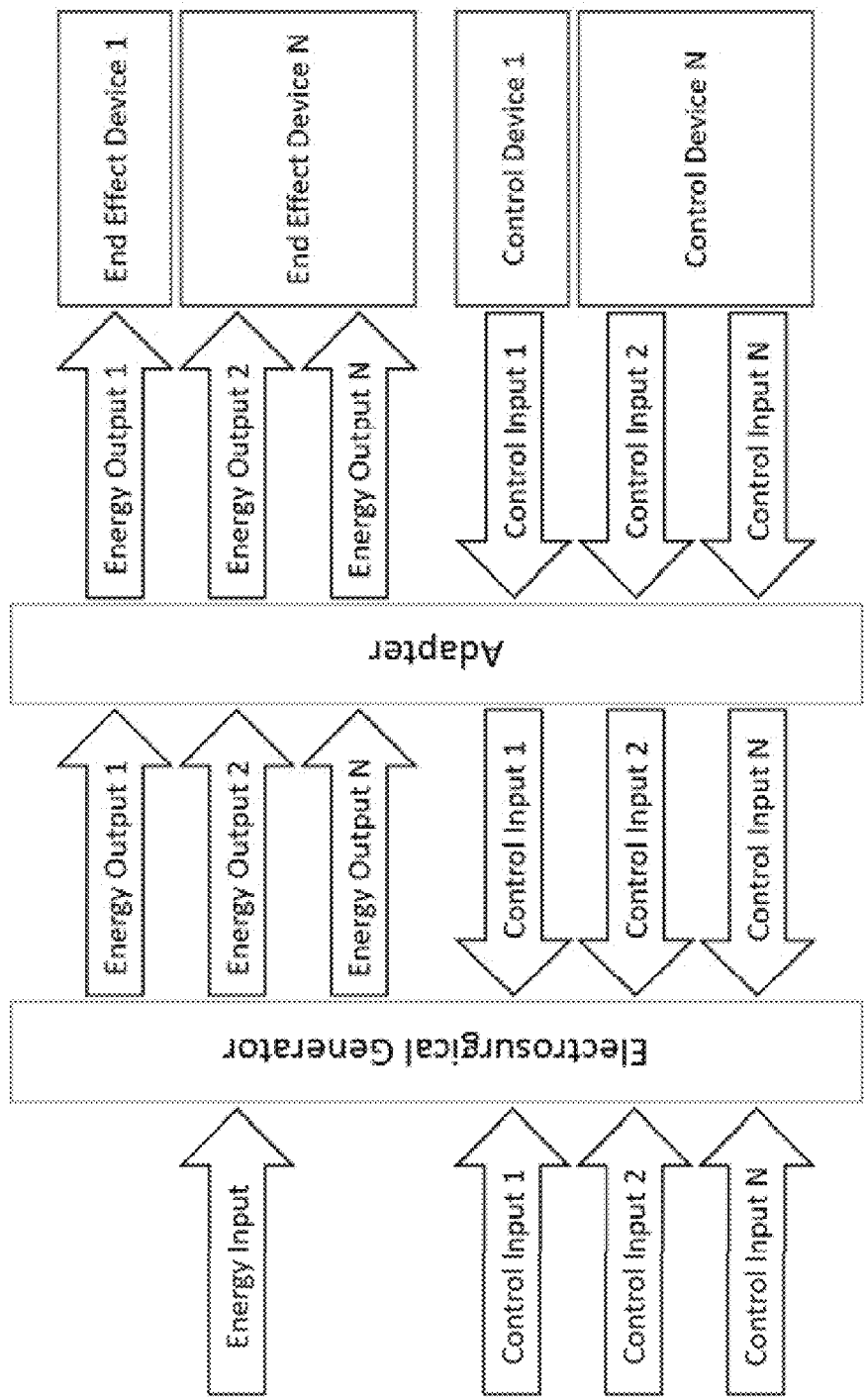
FIG. 1 is an embodiment of an electrosurgical system.

Surgeons often use mechanical, electrosurgical, and ultrasonic techniques in varying amounts to physically help a patient and making these procedures more efficient reduces their inherent risk.

Electrosurgical generators transform readily available electrical energy (i.e. from a wall outlet) into energy usable in electrosurgery with the energy varying in frequency, voltage, current, duty cycle, etc. This transformed energy is then transmitted to tissue through any of number of end effect devices. Transmission of the energy from the generator to the tissue is controlled by any number of control devices. Some forms of energy are preferred for certain functions and procedures. Any form produced by a generator must be efficiently transmitted to the tissue to be acted on and numerous devices perform this function. Different forms or modes are typically transmitted to tissue through unique and separate devices. Devices that can deliver multiple energy forms are advantageous to achieve the optimal tissue effect and expedite procedures.

It is an object of this disclosure to demonstrate novel means of transmitting multiple forms of tissue manipulating energy to a single end-effect device.

End-effect devices that transmit multiple energy forms are well known to the field include "cut" and "coagulation" functions for "monopolar" energy where one, dispersive, electrode is distant from the active, tissue effecting, electrode; and mechanical shearing and coagulation through "bipolar" energy where two electrodes are in proximity.

Devices that can transmit a greater number of energy forms are advantageous to have a specific desired effect on tissue, while minimizing unintended tissue damage and completing the procedure efficiently. One such example is to combine, in a single device, capabilities to transmit monopolar, bipolar, mechanical shearing, and mechanical energy.

The adapter of this disclosure facilitates connection and transmission of these and other energy types.

The adapter can be connected to any form of electrosurgical energy generating or transforming unit and can be controlled by any form of control means, whether presently known or undiscovered today. Any number of tissue effecting devices can be connected to the adapter to deliver one or multiple forms of electrosurgical energy in combination or separately.

Electrosurgical generators typically comprise separate and distinct circuits, and outputs, to deliver the various forms of energy to tissue with each output connected to a separate and unique device. Combination devices capable of delivering multiple forms of electrosurgical energy can be utilized with previously developed generators through an adapter.

The adapter must be able to transmit the energy forms normally generated or transformed to the end effect device and ultimately the tissue to be manipulated. These energy forms can be combined, delivered separately, sequentially, or any variation thereof. The adapter can be configured to be connected to multiple end effect devices, including any number of devices capable of transmitting only one or multiple forms of electrosurgical energy.

An electrosurgical generator is often controlled by a switch, operated by a surgeon, others, or any combination, involved with the procedure. The adapter of this disclosure can be operated by the same, similar, new, or as-of-yet undiscovered or undisclosed means.

The adapter can be made to transmit one form of electrosurgical energy to an end effect device through a single or any number of combination of inputs. The inputs can include switches or sensors activated by surgeons or other personnel, algorithms, or any other form. For example, "monopolar" mode can be activated through a combination of sensors and algorithm that detects that the mechanical configuration of the end effect device is compatible with delivering monopolar energy. A control algorithm can include any number of inputs, for example, amount of time passed, relative position of the device, etc. Monopolar mode can also be selectively activated by a surgeon or any person. Any form of energy mode, including electrosurgical, mechanical, etc., can be selectively activated in these or any other manner and any combination thereof.

One of the main functions of the adapter can be to prevent energy output of one form being transmitted to another output circuit that is not being used, and could be damaged. For example, monopolar can be 10 kV and bipolar is usually below 1 kV (AC peak-peak). The two generator/transformer systems are independent in at least some devices. In some systems, the 1 kV system may not function after delivering 10 kV to its output circuit. In some embodiments, this delivery could damage the output circuit and/or the system, and potentially put the user, system, and patient at risk.

The adapter can be made to deliver multiple forms of energy to a single device separately, sequentially, combined, or any combination. The adapter can be made to deliver only one energy form to devices capable of transmitting only one energy form. The adapter can be made to transmit to the device only energy forms for which the end effect device is capable of transmitting to tissue.

The electrosurgical generator can be activated to generate or transform energy to one specific form when one set of activation input conditions are met. The generator can be activated to transform energy to any one of a specific form when any one of activation input conditions are met. The generator can be activated to transform energy to a different specific form or forms when a different set of activation input conditions are met. The generator can be activated to generate or transform one or multiple energy forms in response to any one or multiple inputs.

The adapter can be activated to transmit energy of one specific form to one end effect device when one set of activation input conditions are met. The adapter can be activated to transmit energy of any one of a specific form to any one of an end effect device when any one of activation input conditions are met. The adapter can be activated to transmit energy to any number of different form or forms to any number of different end effect devices when a different set of activation input conditions are met. The adapter can be activated to transmit one or multiple energy forms in response to any one or multiple inputs.

The adapter can be activated to transmit one input control signal to an electrosurgical generator when one set of activation conditions are met. The adapter can be activated to transmit any one single, multiple, combination, or numerous input control signals to any one or multiple generator input(s) and cause activation of the generator in any form.

In some embodiments, an electrosurgical apparatus is provided. The electrosurgical apparatus can include an adapter connected to an electrosurgical generator. In some embodiments, the adapter is configured to selectively transmit multiple forms of energy through the adapter to a single device. In some embodiments, the adapter can be connected to an independent generator, integrated with the generator, integrated with an activation device, integrated with an output device, or one or any combination of devices. In some embodiments, the adapter-generator-device(s) combination can be selectively activated by any means of input, such as a switch, sensor, thought, remote, robotic, algorithmic, etc. In some embodiments, the input can be of single or any combination of means. In some embodiments, the adapter is configured to selectively transmit energy to any number of end-effect devices. In some embodiments, the end effect devices is configured to transmit any and multiple forms of energy.

In some embodiments, the adapter is configured to selectively transmit multiple forms of energy through the adapter to a single end-effect device. In some embodiments, the adapter is configured to selectively transmit multiple forms of energy through the adapter to one or more end-effect devices. In some embodiments, the adapter is configured to selectively transmit multiple forms of energy through the adapter to a single generator. In some embodiments, the adapter is configured to selectively transmit multiple forms of energy through the adapter back to the generator. In some embodiments, the adapter is configured to selectively transmit multiple forms of energy through the adapter to one or more generators. In some embodiments, the adapter is configured to selectively transmit one or more energy outputs from the electrosurgical generator to one or more end effect devices In some embodiments, the adapter is configured to selectively transmit from the generator to the end effect device. In some embodiments, the adapter is configured to selectively transmit from the end effect device back to the generator. In some embodiments, the adapter is configured to selectively transmit back to the generator.

In some embodiments, the adapter can be used to control the form of energy transmitted to tissue. In some embodiments, the adapter can be configured to receive one input to transmit one output type. In some embodiments, the adapter can be configured to receive one input to transmit any number of output types. In some embodiments, the adapter can be configured to receive a plurality of inputs to transmit one type of output. In some embodiments, the adapter can be configured to receive a plurality of inputs to transmit any number of outputs. In some embodiments, the adapter can have as input any type and number of outputs from the generator. In some embodiments, the adapter can transmit, combine, or transform any form or forms of input into one or more different forms of output. In some embodiments, the adapter can have one or multiple means of output. In some embodiments, the adapter outputs can transmit energy by any means. In some embodiments, the adapter can be configured to select which input(s) are transmitted as output (s). In some embodiments, the adapter can be configured to select input-output transmission by any single or multiple control inputs. In some embodiments, the adapter control inputs can be one or any combination of sensors, switches, algorithms, etc.

FIG. 1 is an embodiment of an electrosurgical system. The system can include an electrosurgical generator. The electrosurgical generator can receive an energy input. In some embodiments, the electrosurgical generator can receive one or more energy inputs.

The system can include an electrosurgical adapter. The electrosurgical adapter can receive one or more energy outputs. The electrosurgical adapter can receive one or more energy outputs from the electrosurgical generator. The electrosurgical generator can send one or more energy outputs (e.g., energy output 1, energy output 2, energy output n).

The system can include an end effect device. The system can include one or more end effect devices (end effect device 1, end effect device n). The one or more end effect devices can receive one or more energy outputs. The one or more end effect devices can receive one or more energy outputs from the electrosurgical adapter (e.g., energy output 1, energy output 2, energy output n). Each end effect device can receive one or more energy outputs from the electrosurgical adapter. The end effect device can receive any form of energy from the adapter through one or multiple wires. The adapter can be configured to be used with and connected to common generator, cable, and end effect devices.

The system can include one or more control devices (control device 1, control device n). The one or more control device can send one or more control inputs. The one or more control device can send one or more control device inputs to the electrosurgical adapter (e.g., control device 1, control device 2, control device n). Each control device can send one or more control inputs to the electrosurgical adapter.

The electrosurgical adapter can receive one or more control inputs (e.g., energy output 1, energy output 2, energy output n). The electrosurgical adapter can send one or more control inputs (e.g., control input 1, control input 2, control input n). The electrosurgical adapter can send one or more control inputs to the electrosurgical generator (e.g., control input 1, control input 2, control input n).

The electrosurgical generator can receive a control input. The electrosurgical generator can receive one or more control inputs (e.g., control input 1, control input 2, control input n). The electrosurgical generator can receive one or more control inputs from the electrosurgical adapter. The electrosurgical generator can receive one or more control inputs from another source. The electrosurgical generator can receive one or more control inputs from the user.

Figure 2:
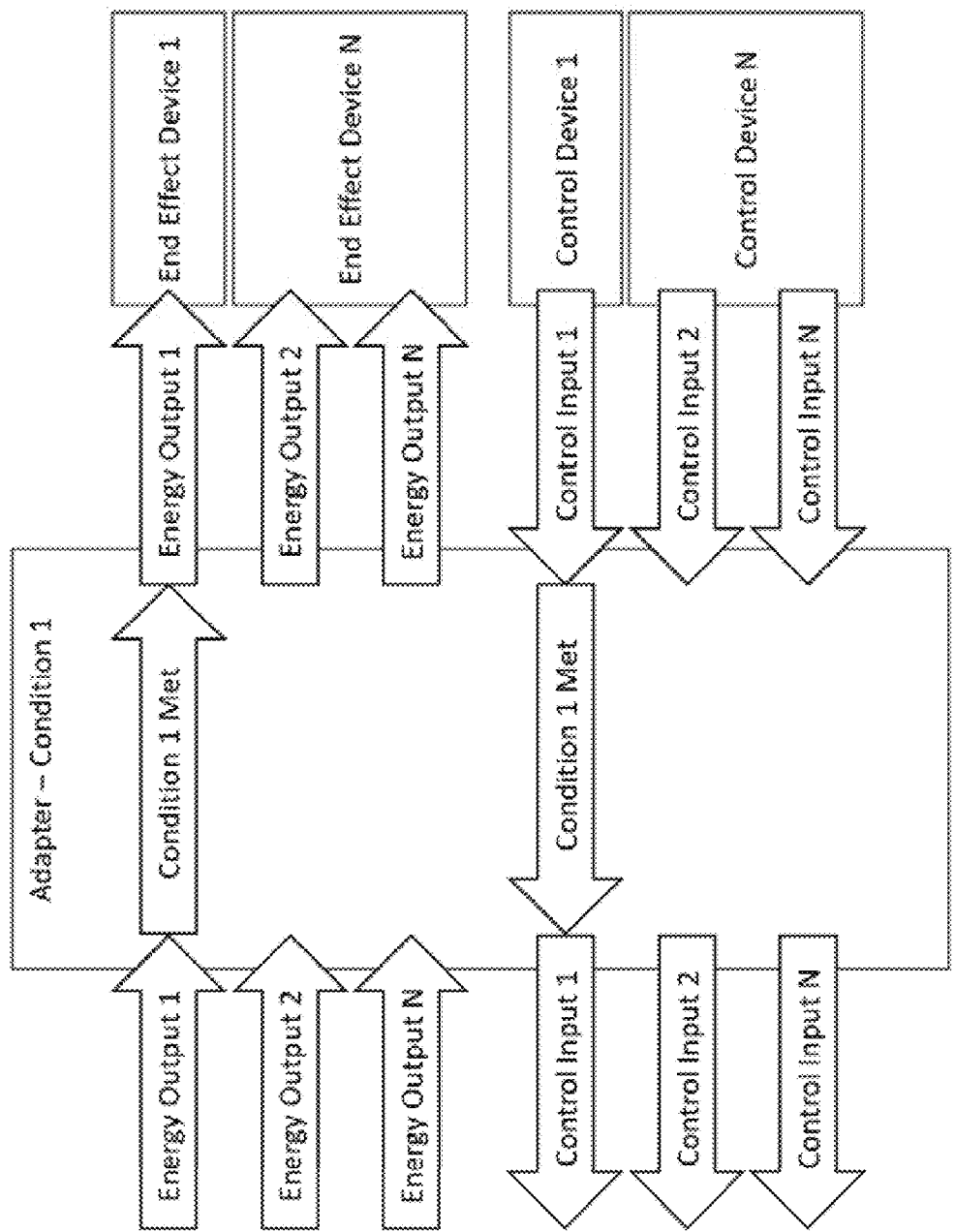
FIG. 2 is an embodiment of an electrosurgical energy adapter in a first condition.

FIG. 2 is an embodiment of an electrosurgical energy adapter in a first condition. The electrosurgical adapter can receive one or more energy outputs (e.g., energy output 1, energy output 2, energy output n). In some embodiments, energy output 1 is received by the electrosurgical energy adapter. In some embodiments, energy output 1 is sent by the electrosurgical generator (not shown). In some embodiments, the electrosurgical energy adapter determines if a condition is met. If condition 1 is met, then the electrosurgical adapter can send an energy output. If condition 1 is met, then the electrosurgical adapter can send an energy output (e.g., energy output 1) to end effect 1.

The electrosurgical adapter can receive one or more control inputs (e.g. control input 1, control input 2, control input). The electrosurgical adapter can receive one or more control inputs from one or more control devices. In some embodiments, control input 1 is received by the electrosurgical energy adapter. In some embodiments, the electrosurgical energy adapter determines if a condition is met. If condition 1 is met, then the electrosurgical adapter can send a control input. If condition 1 is met, the electrosurgical adapter can send a control input (e.g., control input 1). If condition 1 is met, the electrosurgical adapter can send a control input (e.g., control input 1) to the electrosurgical generator (not shown).

Figure 3:
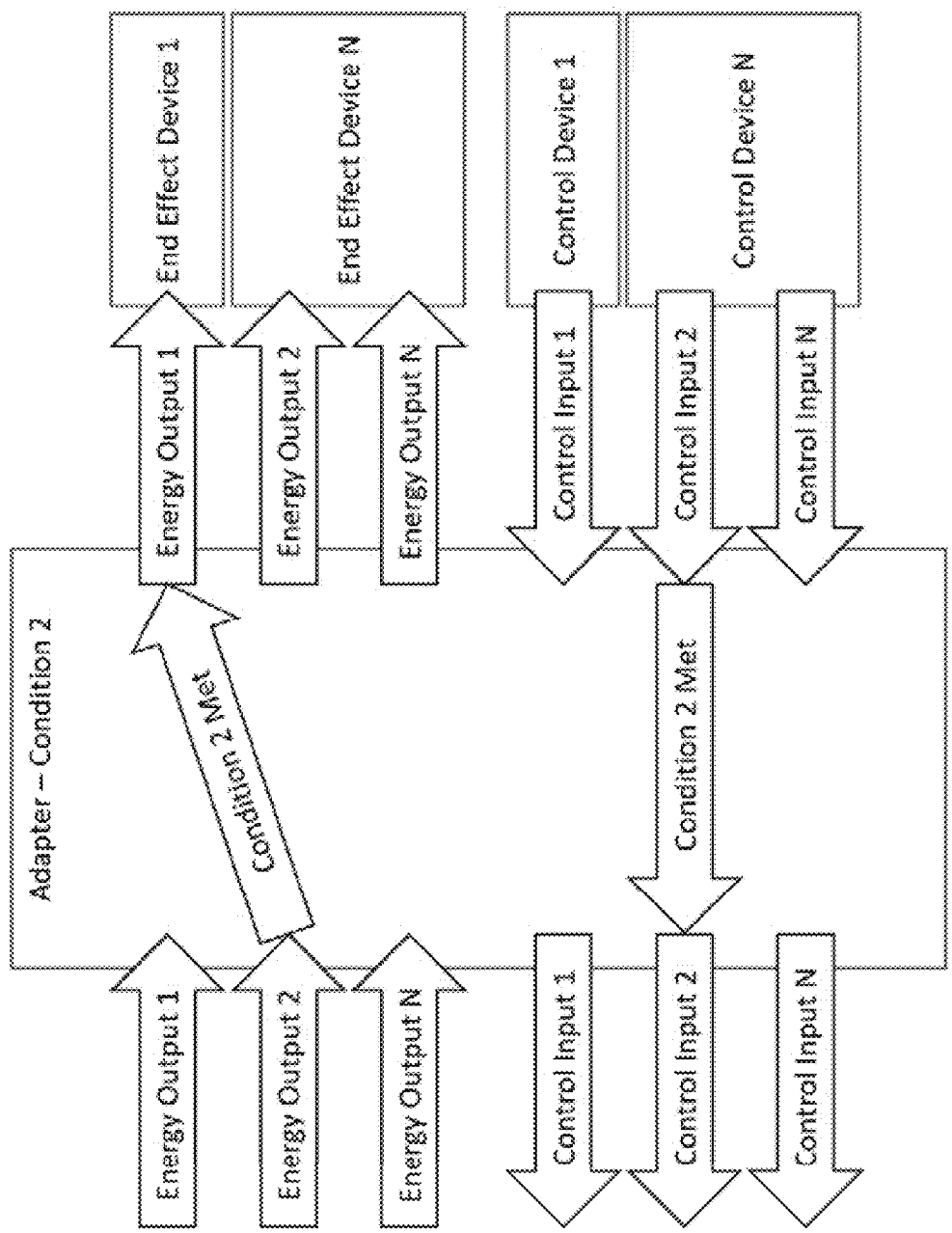
FIG. 3 is an embodiment of an electrosurgical energy adapter in a second condition.

FIG. 3 is an embodiment of an electrosurgical energy adapter in a second condition. The electrosurgical adapter can receive one or more energy outputs (e.g., energy output 1, energy output 2, energy output n). In some embodiments, energy output 2 is received by the electrosurgical energy adapter. In some embodiments, energy output 2 is sent by the electrosurgical generator (not shown). In some embodiments, the electrosurgical energy adapter determines if a condition is met. If condition 2 is met, then the electrosurgical adapter can send an energy output. If condition 2 is met, then the electrosurgical adapter can send an energy output (e.g., energy output 1) to end effect 1. If condition 2 is met, then the electrosurgical adapter can send a different energy output than the energy output received.

The electrosurgical adapter can receive one or more control inputs (e.g. control input 1, control input 2, control input n). The electrosurgical adapter can receive one or more control inputs from one or more control devices. In some embodiments, control input 2 is received by the electrosurgical energy adapter. In some embodiments, the electrosurgical energy adapter determines if a condition is met. If condition 2 is met, then the electrosurgical adapter can send a control input. If condition 2 is met, then the electrosurgical adapter can send a control input (e.g., control input 2). If condition 2 is met, then the electrosurgical adapter can send a control input (e.g., control input 2) to the electrosurgical generator (not shown). If condition 2 is met, then the electrosurgical adapter can send the same control input as the control input received.

Figure 4:
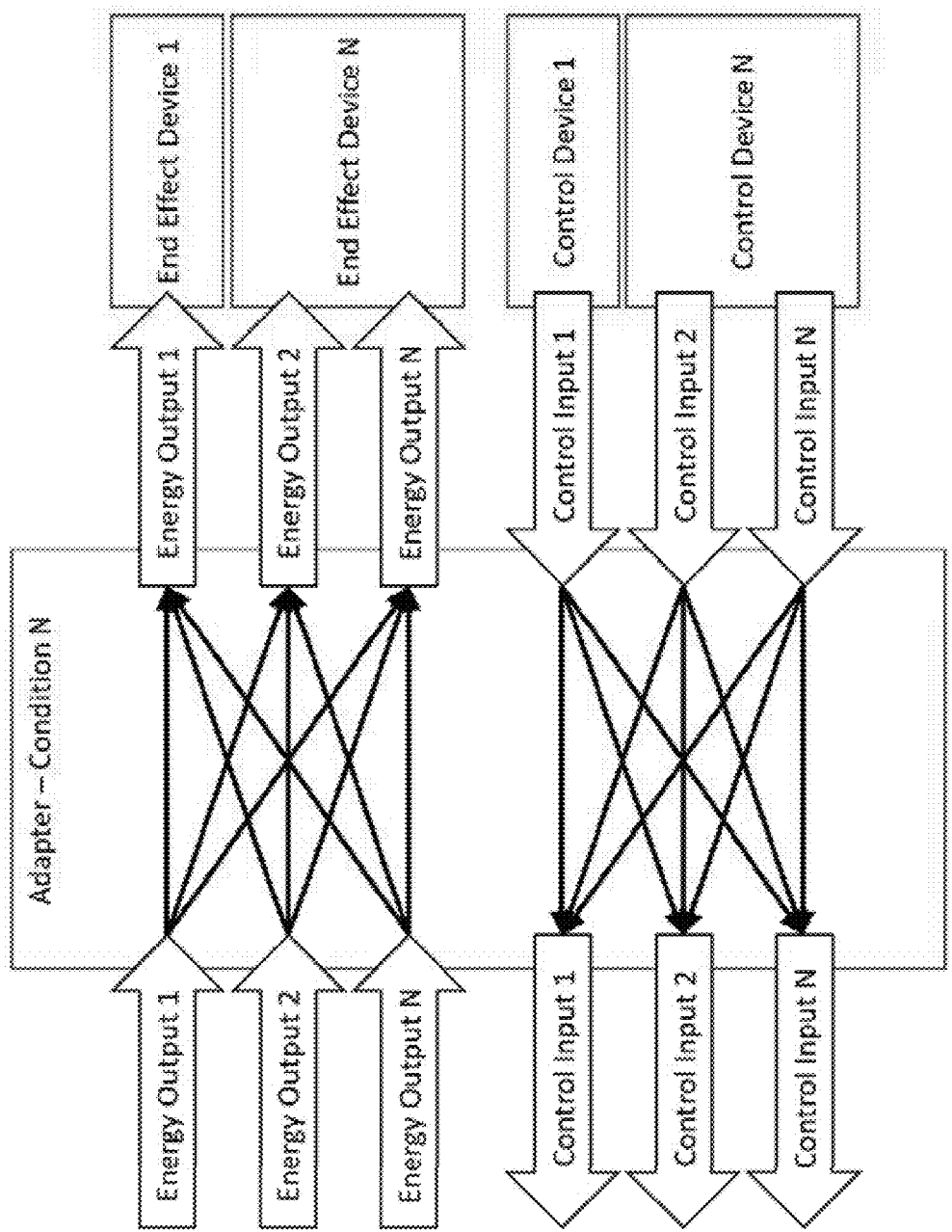
FIG. 4 is an embodiment of an electrosurgical energy adapter in a nth condition.

FIG. 4 is an embodiment of an electrosurgical energy adapter in a nth condition. The electrosurgical adapter can receive one or more energy outputs (e.g., energy output 1, energy output 2, energy output n). In some embodiments, energy output 1, energy output 2, . . . energy output n, is received by the electrosurgical energy adapter. In some embodiments, energy output 1, energy output 2, . . . energy output n are sent by the electrosurgical generator (not shown). In some embodiments, the electrosurgical energy adapter determines if a condition is met. If a condition is met, then the electrosurgical adapter can send an energy output. If one or more conditions are met, then the electrosurgical adapter can send one or more energy outputs (e.g., energy output 1) to one or more end effects. If a condition is met, then the electrosurgical adapter can send a different energy output than the energy output received. If a condition is met, then the electrosurgical adapter can send the same energy output than the energy output received. If a condition is met, then the electrosurgical adapter can send an energy output 1 to end effect 1, energy output 2 to end effect 2, energy output n to end effect n, and/or any combination of these outputs.

The electrosurgical adapter can receive one or more control inputs (e.g. control input 1, control input 2, . . . control input n). The electrosurgical adapter can receive one or more control inputs from one or more control devices. If condition n is met, the electrosurgical adapter can send a control input. In some embodiments, control input 1, control input 2, . . . control input n are received by the electrosurgical energy adapter. In some embodiments, the electrosurgical energy adapter determines if one or more conditions are met. If a condition is met, then the electrosurgical adapter can send an control inputs. If one or more conditions are met, then the electrosurgical adapter can send one or more control inputs (e.g., control input 1). If a condition is met, then the electrosurgical adapter can send a different control input than the control input received. If a condition is met, then the electrosurgical adapter can send the same control input than the control input received. If a condition is met, then the electrosurgical adapter can send the control input 1, control input 2, . . . control input n.

Surgeons often use mechanical, electrosurgical, and ultrasonic techniques in varying amounts to physically help a patient and making these procedures more efficient reduces their inherent risk.

Electrosurgical generators transform readily available electrical energy (i.e. from a wall outlet) into energy usable in electrosurgery with the energy varying in frequency, voltage, current, duty cycle, etc. This transformed energy is then transmitted to tissue through any of number of end effect devices. Transmission of the energy from the generator to the tissue is controlled by any number of control devices. Some forms of energy are preferred for certain functions and procedures. Any form produced by a generator must be efficiently transmitted to the tissue to be acted on and numerous devices perform this function. Different forms or modes are typically controlled through a unique and dedicated control through physical, wired, connections.

It is an object of this disclosure to demonstrate novel means of transmitting multiple forms of electrosurgical generating energy control.

Electrosurgical energy control by numerous forms are well known to the field and include switches and sensors. The controls commonly used are directly wired to the electrosurgical generator and with a large, cumbersome form that is not ergonomically advantageous to the user. These characteristics limit the users' physical position and stance with regard to the patient, and slows the procedure when positional changes are required.

Devices that allow a user to obtain an optimal ergonomic position while simultaneously maintaining control of the electrosurgical system are advantageous to expedite the procedure, minimizing patient risk and procedural related expense.

The control can be configured to take as input any output of a user. The control can consist of any one, numerous, or combination of switches or sensors. The control can take as input any signal generated by a user (i.e. position, force, thought, etc.) and in any combination with other means (algorithm, timer, device position, etc.). The user output can be associated with one or any number of digits, limbs, muscles, etc.

A control unit connected to an electrosurgical generator can be separate, integrated with, or any combination. A control unit connected to a user can be separate from or integrated with any one or numerous sensors. A control unit can be connected to or integrated with any end effect device.

A control unit connected to a user can have as input any one or numerous inputs. Inputs to the control system can included switches, sensors, algorithms, etc. Input sensors connected with a control unit can take any form. Input sensors can be integrated with or attached to any number of garments. Input sensors can be temporarily or permanently affixed to a user. Input sensors can translate the users intentions into a control signal.

An electrosurgical control system can consist of two or more units that are connected in any combination. The control units can be connected to each other in any form with at least one unit connected without cables. At least one of the control units can be connected to and facilitate control of the electrosurgical generator. At least one of the units can be connected to and receive control from the user. The electrosurgical energy control units can utilize any communication protocol or energy form.

The electrosurgical control system can cause any change in the electrosurgery energy generating system and can include mode, energy form, energy level, etc. In some embodiments, an electrosurgical apparatus is provided. The electrosurgical apparatus can include a control connected to an electrosurgical generator. In some embodiments, the control is configured to selectively transmit control instructions to the electrosurgical system. In some embodiments, the control is configured to integrate with an output of a user. In some embodiments, the control is integrated with the user in any position. In some embodiments, the control connects any number of elements of a user's outputs to the electrosurgical system. In some embodiments, the control connects the user intentions to the electrosurgical system without cables. The connection can make use any protocol (Wifi, Bluetooth, etc.).

In some embodiments, the control can take as user input any switch. In some embodiments, the control can take as user input any sensor. In some embodiments, the control can have as input any combination of switches, sensors, algorithms, etc. In some embodiments, the control can connect to the electrosurgical system without wires. In some embodiments, the control can connect to the electrosurgical system through a dedicated connection. In some embodiments, the control can connect to the electrosurgical system through numerous connections. In some embodiments, the control can have as output instructions understood by the electrosurgical system.

In some embodiments, the control can be composed of any number of user inputs. In some embodiments, the sensor can be integral with, embedded in, associated with a garment (sock, glove, shoe, insole, etc.). In some embodiments, the sensor data or readings can be transmitted wirelessly to a switch. In some embodiments, a sensor signal (or multiple sensors and signals) can be processed before and/or after wireless transmission. In some embodiments, a plurality of sensors can be activated simultaneously. In some embodiments, a plurality of sensors can detect and output a plurality of readings. In some embodiments, a combination of readings within a range can produce a particular output. In some embodiments, a second combination of readings within a range can produce a second different output. In some embodiments, any number of combinations of readings, each within a range, can each produce a distinct output. In some embodiments, any number of combinations of continuous (through time and/or relative pressure or position differences) readings can produce a continuous output. In some embodiments, the wireless transmitter can be permanently paired or paired by user input. In some embodiments, the switch can be allowed to be activated only while the sensor is in a particular range or can be activated or inactivated in any or no range of distance. In some embodiments, the system includes a wired connection for a standard wired footswitch (redundant backup).

Figure 5:
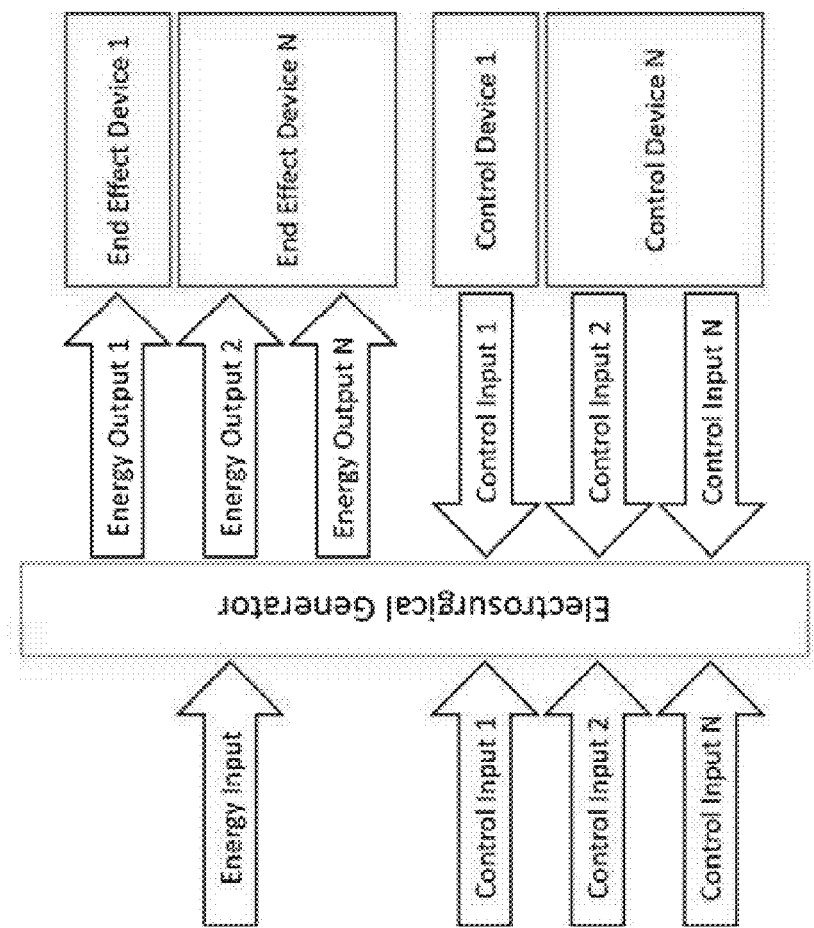
FIG. 5 is an embodiment of an electrosurgical system.

FIG. 5 is an embodiment of an electrosurgical system. The system can include an electrosurgical generator. The electrosurgical generator can receive an energy input. In some embodiments, the electrosurgical generator can receive one or more energy inputs.

The system can include an end effect device. The system can include one or more end effect devices (end effect device 1, end effect device n). The one or more end effect devices can receive one or more energy outputs. The one or more end effect devices can receive one or more energy outputs from the electrosurgical generator (e.g., energy output 1, energy output 2, energy output n). Each end effect device can receive one or more energy outputs from the electrosurgical adapter.

The system can include one or more control devices (control device 1, control device n). The one or more control device can send one or more control inputs. The one or more control device can send one or more control device inputs to the electrosurgical generator (e.g., control device 1, control device n). Each control device can send one or more control inputs to the electrosurgical adapter.

The electrosurgical generator can receive a control input. The electrosurgical generator can receive one or more control inputs (e.g., control input 1, control input 2, control input n). The electrosurgical generator can receive one or more control inputs from another source. The electrosurgical generator can receive one or more control inputs from the user.

Figure 6:
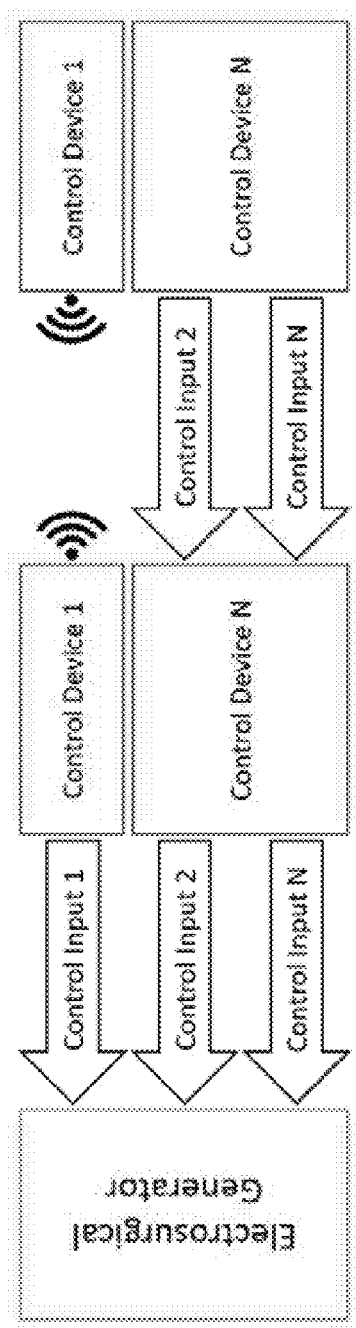
FIG. 6 is an embodiment of an electrosurgical system.

FIG. 6 is an embodiment of an electrosurgical system. The system can include an electrosurgical generator. The electrosurgical generator can receive a control input. The system can include one or more control devices (control device 1, control device n). The one or more control device can send one or more control inputs. The first set of control device can send one or more control device inputs to the electrosurgical generator (e.g., control device 1, control device n). Each control device can send one or more control inputs to the electrosurgical adapter.

The system can include one or more additional control devices (control device 1, control device n). The one or more control device can send one or more control inputs. The second set of control device can send one or more control device inputs to the first set of control devices. Each control device of the second set can send one or more control inputs to the first set of control devices. Each control device of the second set can send one or more control inputs to the first set of control devices wirelessly. Each control device of the second set can send one or more control inputs to the first set of control devices through a wired or direct connection.

In some embodiments, the end effect device can function as a control device. The end effect device can send a signal to the adapter or generator. The end effect device can provide information about particular mechanical, electrical, or position status. The end effect device can provide control signals. The end effect device can provide a control input to the adapter. The end effect device can provide a control input to the generator.

Figure 7:
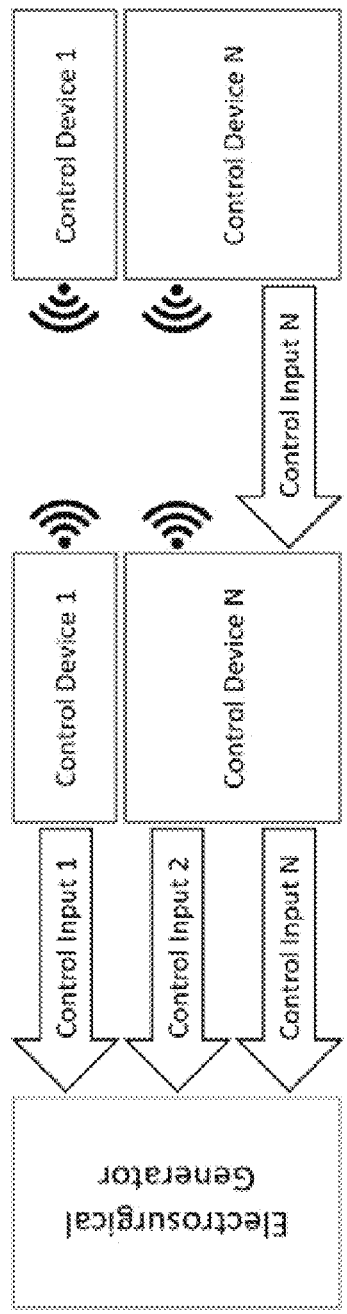
FIG. 7 is an embodiment of an electrosurgical system.

FIG. 7 is an embodiment of an electrosurgical system similar to FIG. 6. Each control device of the second set can send one or more control inputs to the first set of control devices. Each control device of the second set can send one or more control inputs to the first set of control devices wirelessly. Each control device of the second set can send one or more control inputs to the first set of control devices through a wired or direct connection. Each control device of the second set can send in one or more transmission types.

Figure 8:
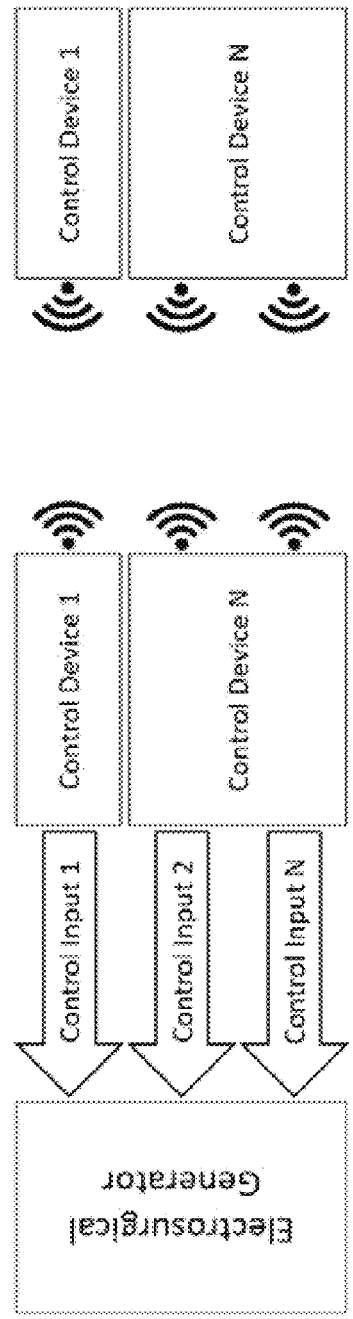
FIG. 8 is an embodiment of an electrosurgical system.

FIG. 8 is an embodiment of an electrosurgical system similar to FIG. 6. Each control device of the second set can send one or more control inputs to the first set of control devices. Each control device of the second set can send one or more control inputs to the first set of control devices wirelessly.

Figure 9:
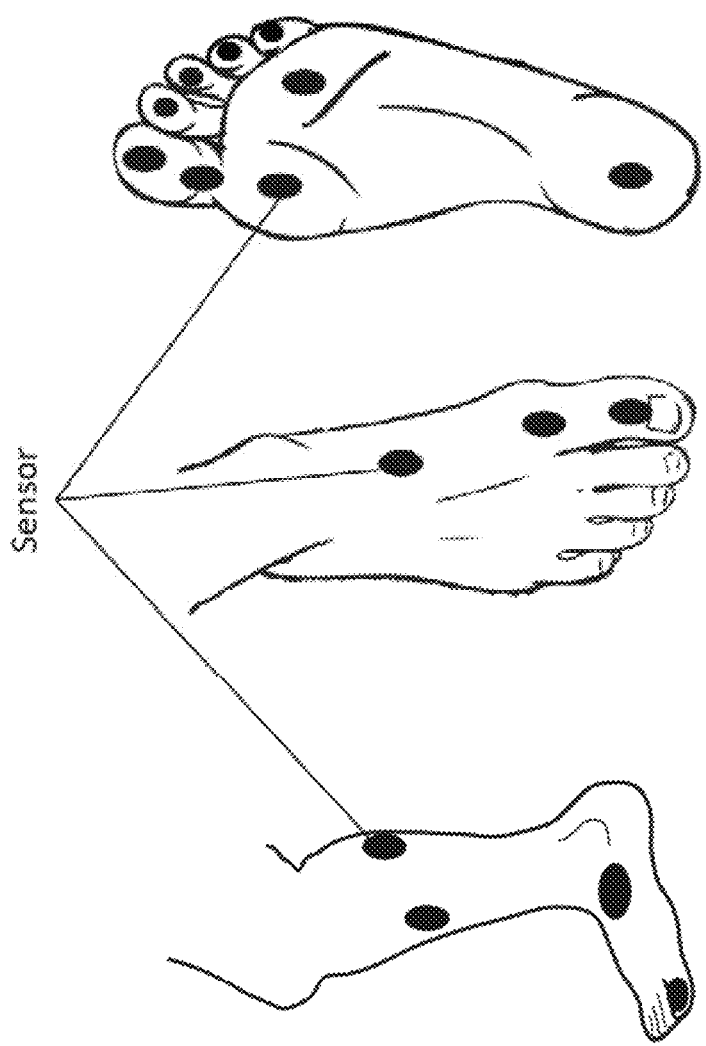
FIG. 9 is an embodiment of sensors on the feet and leg of a user.
Figure 10:
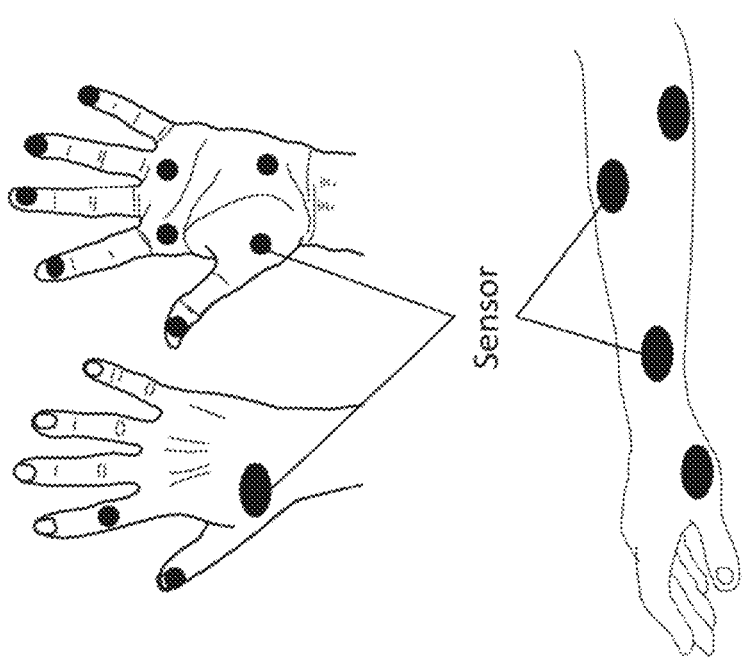
FIG. 10 is an embodiment of sensors on the hand and arm of a user.

FIG. 9 is an embodiment of sensors on the feet and leg of a user. FIG. 10 is an embodiment of sensors on the hand and arm of a user. The user can provide a control input. The user can provide a control input in any position. The user can provide a control input with any portion of the body of the user. The user can provide a control input using any number of sensors. The user can provide a control input using any number of elements. The user can provide a control input to the electrosurgical system. The user can provide a control input to the electrosurgical generator. The user can provide a control input to a control device. The user can provide a control input to a control device of the first set of control devices. The user can provide a control input to a control device of the second set of control devices.

The user can provide a control input by movement of any portion of the body. The body portion can be a foot. The body portion can be a toe. The body portion can be a leg. The body portion can be a shin. The body portion can be a hand. The body portion can be an arm. The body portion can be a finger. The body portion can be a wrist. The body portion can be a head. The user can provide a control input by movement of a body portion connected to a sensor. The one or more sensors can be coupled with a garment. The one or more sensors can be integral with a garment. The garment can be a sock. The garment can be a glove. The garment can be a shoe. The garment can be an insole. The garment can be a sticker. The garment can detect position, length, force, capacitance, sound or any other input.

The user can control a switch. The user can provide a control input by a user input device. The user can provide a control input by a keypad. The user can provide a control input by a joystick. The user can provide a control input by a mouse. The user can provide a control input by software. The user can provide a control input by an algorithm. The user can provide a control input by any combination herein.

The sensor data can be transmitted wirelessly. The sensor data can be transmitted through a wired connected. The sensor data can be transmitted to a switch. The user can control the switch. A component of the system can control the switch. An adapter can control the switch. The sensor data can be processed before transmission. The sensor data can be processed after transmission. The sensors can be activated independently. The sensors can be activated simultaneously. Each sensors can detect and output a reading. The two or more sensors can detect and output a reading. The sensors can transmit in real-time. The sensors can transmit continuously. Each sensor can include a transmitter. The plurality of sensors can correspond to a single transmitter.

The user can provide a control input without wires. The user can provide a control input wirelessly. The user can provide a control input through a dedicated connection. The user can provide a control input through numerous connections. The user can provide a control input through any instruction network. The user can provide a control input as any type of instructions. The user can provide a control input in any format understood by the electrosurgical system. The user can provide one or more control inputs. The user can provide one or more of the same control inputs. The user can provide one or more different control inputs.

It is an object of this disclosure to demonstrate novel end effect device capable of efficiently delivering multiple types of energy.

Recent advances have demonstrated capabilities of single devices to delivery multiple different forms of energy to tissue and include mechanical, electrical, ultrasonic, etc. Unique and separate components are often required to deliver each of these energy types to achieve the desired tissue effect. Components able to perform multiple and numerous functions are advantageous to optimize procedural workflow while reducing patient risk and costs.

Tissue effecting components may have some portions or surfaces optimized to transfer electrical energy. Tissue effecting components may have other portions or surfaces optimized to transfer mechanical energy, such as compression or shearing. Tissue effecting components may have some or any portion of any surface optimized to transfer any portion of electrical or mechanical energy.

Shearing of tissue involves interference of blades at a focal point. Blade interference must be sufficient to shear the tissue and not allow it to pass, unaffected, between the blades. Components that produces shearing action in addition to transferring other forms of energy must be able to transition between various modes without excessive stress to the user or device.

Scissor blades often rotate about an axis across a plane where each of the scissor blades crosses the plane, causing interference with the opposing blade. Scissor blades in surgical devices capable of delivery other forms of energy, must have their collective rotation axis relaxed to allow other movements and facilitate compression or delivery of electrosurgical energy. This axis must be re-established to allow the device to continue its shearing function. Along with the axis, interference between the blades must also be selectively relaxed and re-established.

One method of allowing selective scissor blade axis and interference relaxation and re-establishment is by allowing the scissor axis to be established in only the shearing mode. The axis can be relaxed by changing the axis angle of one blade relative to the blade of the other axis, while keeping some portion of the blades in proximity. Another method is to allow the axis to be removed entirely from the other blade. The axis can then be re-established when the blades are approximated. Interference between the blades can be minimized in the neutral position while the axis is re-established, minimizing forces needed to generate shearing blade interference.

Shearing blades that cross the plane while the two blades are aligned generate interference as the two scissor blades are opened (rotationally moved in opposing directions across the central plane. Shearing blades that cross the central plane while the blades are open can maintain interference for any given level or distance before relaxing near alignment. Each blade may have sufficient relief for the portions of the opposing blade crossing the central plane.

In some embodiments, an electrosurgical apparatus is provided. The electrosurgical apparatus can include an end effect device capable of delivering at least mechanical and electrical energy to tissue. In some embodiments, the end effect device consists of at least two components directly delivering said energy forms to tissue. In some embodiments, the two components are formed such that movement toward and away from a central plane is selectively restricted. In some embodiments, the two components are formed such that movement along the central plane is selectively restricted. In some embodiments, the two components are formed such that movement across the central plane is selectively restricted. In some embodiments, the two components are formed such that movement along and away/toward the central plane is simultaneously restricted. In some embodiments, the two components are formed such that movement in one direction relative to the central plane is restricted. In some embodiments, the two components are formed such that movement in two directions relative to the central plane is simultaneously restricted. In some embodiments, the two components are formed such that movement in two skewed directions relative to the central plane is simultaneously restricted. In some embodiments, the two components are formed such that movement in two perpendicular directions relative to the central plane is simultaneously restricted. In some embodiments, the two components are formed such that movement in at least the toward/away direction is restricted. In some embodiments, the two components are formed such that movement in at least the along/across direction is restricted.

In some embodiments, the two components are formed such that a portion of each of the components protrude to the other side of a central plane. In some embodiments, approximating the two components to the central plane allows selective restriction of movement away from the central plane. In some embodiments, opposing movement along the same central plane produces interference between the two components. In some embodiments, the two components of the end effect device have one or more surfaces compatible with transmission of electrosurgical energy. In some embodiments, the two components of the end effect device have one or more surfaces compatible with transmission of pinching mechanical energy. The two components of the end effect device have one or more surfaces compatible with transmission of shearing mechanical energy.

Figure 11:
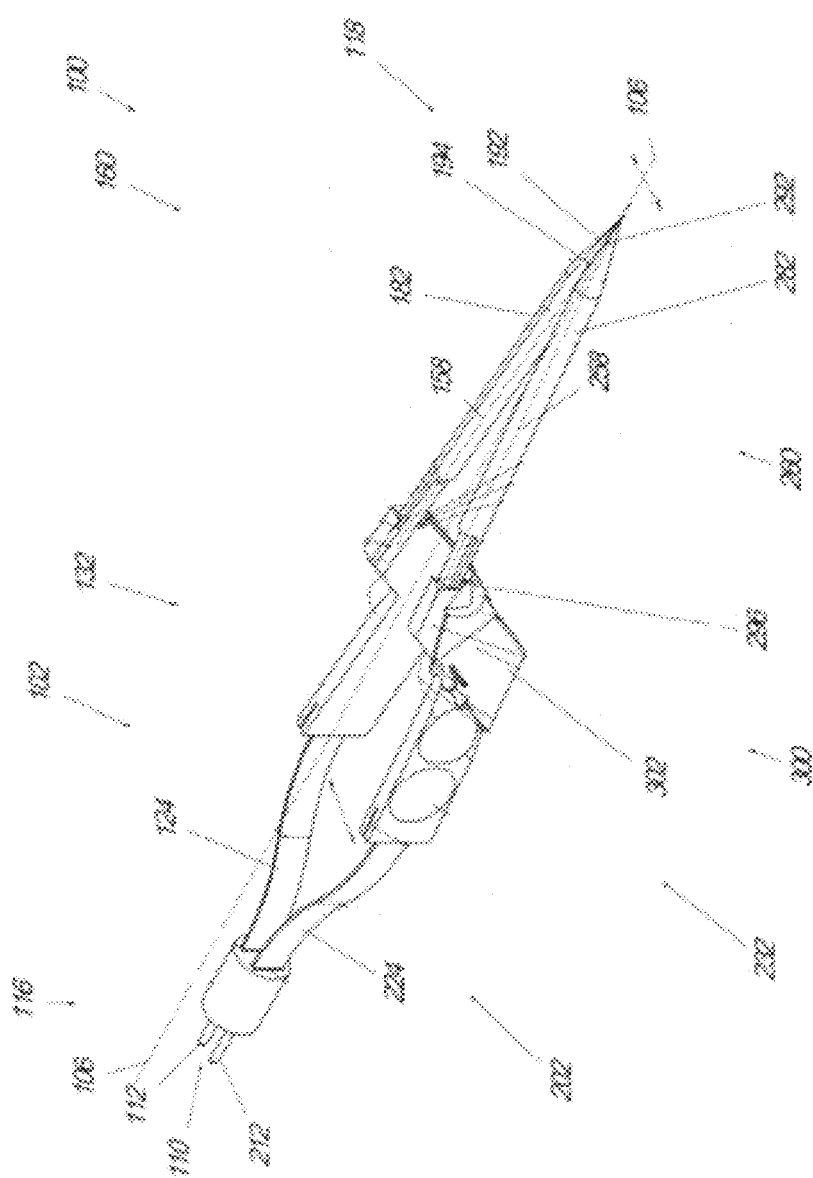
FIG. 11 is an embodiment of a surgical multitool.

With reference to FIGS. 11, a hand tool 100 is shown. The hand tool 100 can also be referred to as a surgical multi-tool. The hand tool 100 comprises two sections: a left section 102 and a right section 202. The left section 102 interacts with the right section 202 to perform one or more functions, such as operating as forceps, scissors, and probe. The surgical hand tool 100 can transition between functional configurations. The surgical hand tool can operate as forceps, which can also be referred to as the forceps configuration, with the left tip 160 and the right tip 260 providing the grasping ends of the forceps. In this and other configurations, the surgical hand tool 100 can also include electrodes. For example, the surgical hand tool of FIG. 11 can function as electrocautery bipolar forceps. The surgical hand tool can further be configured to operate as scissors, which can also be referred to as the scissors configuration. The tips 160, 260 slide and pivot relative to each other to cut tissue. The scissors can be utilized to more quickly cut tissue. The surgical hand tool can further be configured to operate as a probe, which can also be referred to as the probe configuration. The multiple configurations allow for the use of multiple surgical techniques at the discretion of the user. Other functional configurations are possible. U.S. Pat. No. 9,943,327 issued Apr. 17, 2018 is hereby incorporated by reference in its entirety. Additional details of multi-tools can be found in U.S. Pat. No. 9,943,327 issued Apr. 17, 2018, which is incorporated by reference in its entirety. The surgical hand tools can have a plurality of configurations including a forceps configuration, a probe configuration and a scissors configuration. In some embodiments, the surgical tool has a first configuration wherein the first and second tips operate as forceps. In some embodiments, the surgical tool has a second configuration wherein the first and second tips operate as scissors. In some embodiments the surgical tool has a third configuration in which the first and second tips operate as a probe. In some embodiments, rotation of the first tip and the second tip within their respective recesses transitions the surgical tool between the first, second, and third configurations. In some embodiments, the probe is configured for monopolar electrocautery, monopolar detection, and monopolar stimulation. In some embodiments, the forceps configuration includes a bipolar electrocautery forceps configuration. In some embodiments, the scissors configuration includes a microscissors configuration. In some embodiments, the scissors configuration, the forceps configuration, and the probe configuration are mutually exclusive functional configurations. The multiple configurations allow for the use of multiple surgical techniques at the discretion of the user. Other functional configurations are possible.

FIG. 11 shows the hand tool 100 in the intermediate configuration. In order to change configurations, the handles 132, 232 are moved toward each other. The user applies a force to overcome the biasing force of the springs 124, 224. The internal surface of the handles 132, 232 can abut. The left tip 160 and the right tip 260 can be brought together. The tips 160, 260 can abut. The internal flat surfaces can abut. The left tip axis 158 and the right tip axis 258 can align along the longitudinal axis 106. The protrusion can engage the recess 194. The intermediate configuration permits the transition from the forceps configuration to the scissors configuration. The intermediate configuration permits the transition from the scissors configuration to the forceps configuration. In some embodiments, the intermediate configuration is the probe configuration. In some embodiments, the hand tool 100 transitions from the forceps configuration to the probe configuration to the scissors configuration. In some embodiments, the hand tool 100 transitions from the scissors configuration to the probe configuration to the forceps configuration. In some embodiments, the probe configuration is not an intermediate configuration. In some embodiments, the hand tool 100 transitions from the scissors configuration to the forceps configuration to the probe configuration. In some embodiments, the hand tool 100 transitions from the forceps configuration to the scissors configuration to the probe configuration. In some embodiments, the intermediate configuration can permit the transition from the scissors configuration to the probe configuration. In some embodiments, the intermediate configuration can permit the transition from the probe configuration to the scissors configuration. In some embodiments, the intermediate configuration can permit the transition from the forceps configuration to the probe configuration. In some embodiments, the intermediate configuration can permit the transition from the probe configuration to the forceps configurations. The intermediate position permits the transition from the scissors configuration to the probe configuration, the probe configuration to the scissors configuration, the forceps configuration to the probe configuration, and the probe configuration to the forceps configurations.

As shown in FIG. 11, the hand tool 100 can include a mechanism 300 that enables the user to transition between the forceps configuration, the scissors configuration, and the probe configuration. In the illustrated embodiment, the mechanism 300 is located on the right handle 232. The mechanism 300 can include a slide 302. The slide 302 is capable of sliding upward and downward relative to the right handle 232. The mechanism 300 can have a first position, an intermediate position, and a second position. The first position can correspond to forceps configuration. The second position can correspond to the scissor configuration. The intermediate position can correspond to the probe configuration. In some embodiments, the intermediate position is in between the first position and the second position. In some embodiments, the hand tool 100 transitions from the forceps configuration, to the probe configuration, then to the scissors configuration by movement of the mechanism 300 in one direction. In some embodiments, the hand tool 100 transitions from the scissors configuration, to the probe configuration, then to the forceps configuration by movement of the mechanism 300 in the opposite direction. In some embodiments, the hand tool 100 transitions between the configurations in any order. In some embodiments, the positions of the mechanism 300 are in any order. The functional configuration of the hand tool 100 is selected by the user by manipulating the mechanism 300. The user can slide a finger to move the slide 302. The user can manipulate the mechanism 300 while holding the hand tool 100. The slide 302 can change the position of the slot relative to the pin 296. The mechanism 300 can exert a force on the pin 296 to rotate the pin 296. In the illustrated embodiment, an edge of the slot of the mechanism 300 can act on the pin 296. The rotation of the pin 296 can rotate both tips 160, 260. The tips 160, 260 can rotate approximately 90° as the hand tool 100 is transitioned between the forceps configuration and the scissors configuration. Other ranges of motion of the tips 160, 260 are possible (e.g., 80°, 85°, 90°, 95°, 100°). Both tips 160, 260 can rotate the same direction.

The hand tool 100 does not need to be removed from the surgical site to switch configurations. The mechanism 300 can be manipulated while the tips 160, 260 remain within the surgical site. The hand tool 100 requires the user to collapse the hand tool 100 in the intermediate configuration. This requires less space than either the forceps configuration or the scissors configuration. In some embodiments, once in the intermediate configuration, the user can transition between the forceps configuration and the scissors configuration. In some embodiments, once in the intermediate configuration, the user can transition between the forceps configuration, the scissors configuration, and the probe configuration. The hand tool 100 does not require any large movements to switch configurations.

The hand tool 100 can include a probe configuration. In some embodiments, the hand tool 100 functions as a unipolar probe in the probe configuration. In some embodiments, the hand tool 100 functions as a bipolar probe in the probe configuration. In some embodiments, the hand tool 100 functions as a multipolar probe in the probe configuration. The hand tool 100 can include the left handle 132 and the right handle 232. The hand tool 100 can include the left tip 160 and the right tip 206. The left handle 132 and the right handle 232 can retain the left tip 160 and the right tip 260 as described herein. The left handle 132 and the right handle 232 can be brought together in order to transition the hand tool 100 between the forceps configuration and the scissors configuration as described herein.

In some embodiments, in the probe configuration, the handles 132, 232 are moved toward each other. In some embodiments, the left handle 132 is moved toward the right handle 232. In some embodiments, the right handle 232 is moved toward the left handle 132. In some embodiments, the user applies a force to overcome the biasing force of the springs 124, 224. In some embodiments, the internal surface of the handles 132, 232 can abut. In other embodiments, the internal surface of the handles 132, 232 are near each other but do not abut in the probe configuration. In some embodiments, some portion of the handles 132, 232 may approximate or abut. In some embodiments, any portion of the handles 132, 232 may approximate or abut. In some embodiments, the hand tool 100 is designed to limit the collapse in one or a couple specific areas to provide smooth movement and prevent over travel. The hand tool 100 has one or more portions to approximate or abut along the length of the hand tool. In some embodiments, the hand tool 100 is designed to provide smooth movement. In some embodiments, the hand tool 100 is designed to provide smooth movement during collapse to the probe configuration. In some embodiments, the hand tool 100 is designed to prevent over travel. In some embodiments, the hand tool 100 is designed to prevent over travel during collapse to the probe configuration. In some embodiments, the left tip 160 and the right tip 260 can be brought together. In some embodiments, the tips 160, 260 can abut. In other embodiments, the left tip 160 and the right tip 260 are near each other but do not abut in the probe configuration. The internal flat surfaces 184, 284 can abut. In some embodiments, the left tip axis 158 and the right tip axis 258 can align in the probe configuration. In other embodiments, the left tip axis 158 and the right tip axis 258 do not align in the probe configuration. In some embodiments, the protrusion 294 can engage the recess 194 in the probe configuration. In some embodiments, the probe configuration is a low-profile configuration. In some embodiments, one or more components of the left section 102 are brought together or abuts one more components of the right section 202.

In some embodiments, the hand tool 100 has an intermediate position lockout. The intermediate position lockout can include the mechanism configured to maintain the intermediate position or probe position. The mechanism of the hand tool 100 can operate to lockout handles 132, 232 from separating unless completely in either the scissors configuration or the forceps configuration.

The hand tool 100 in the probe configuration can conduct an electrical signal or current. The hand tool 100 in the probe configuration can allow monopolar cutting, cauterization, and fulguration. The hand tool 100 in the probe configuration can allow hardware detection. The hand tool 100 in the probe configuration can allow nerve, muscle, and tissue stimulation. The hand tool 100 in the probe configuration can allow nerve, muscle, tissue, and implant detection. The hand tool 100 in the scissors configuration can allow nerve, muscle, and tissue stimulation. The hand tool 100 in the scissors configuration can allow nerve, muscle, and tissue detection. The hand tool 100 in the forceps configuration can allow nerve, muscle, and tissue stimulation. The hand tool 100 in the forceps configuration can allow nerve, muscle, and tissue detection. The surgical hand tool can include electrodes as described herein. The left tip 160 can include an electrode 192. The right tip 260 can include an electrode 292. In the probe configuration, one of the electrodes 192, 292 or another electrode of the hand tool 100, 1000 can be supplied with electrical current. One of the tips 160, 260 can include electrode for monopolar electrosurgery. The electrode can be located on the longitudinally extending portion 182, 282. The electrode can be located on an external surface of the tips 160, 260. The electrode can be located on an internal surface of the tips 160, 260, for instance the flat surfaces 184, 284. The electrode can be configured for cauterization, hemostasis, and tissue dissection.

In some embodiments, while in the unipolar probe configuration, the hand tool 100 can be used as a probe. In some embodiments, the device can be used for probe dissection. In some embodiments, the device can be used for blunt dissection. In some embodiments, while in the unipolar probe configuration, electrical energy can be applied to the hand tool 100, 1000 to facilitate unipolar cauterization, ablation, hardware detection, tissue stimulation (nerve, muscle, etc.) or other functions. In some embodiments, the while in any configuration, the device may transmit energy intended for tissue manipulation.

In some embodiments, the forceps configuration can operate as electrocautery forceps. In some embodiments, the forceps configuration can operate as bipolar electrocautery forceps. In some embodiments, the forceps configuration can operate as monopolar electrocautery forceps. The user could use the hand tool 100 in the forceps configuration as a two-bladed probe. The user can deliver monopolar energy. One of the tips 160, 260 can include electrode for monopolar electrosurgery. The user can deliver bipolar energy. Both of the tips 160, 260 can include electrode for bipolar electrosurgery. In some embodiments, the most common way to deliver energy would be to have the blades together in the intermediate or probe configuration.

For instance, the hand tool 100 can include one or more electrodes located on the tips of the hand tool. The hand tool 100 can be designed to supply electrical energy to the electrodes. In some embodiments, the hand tool 100 can optionally include an electrical connection 110. The electrical connection 110 can include a left lead 112 and a right lead 212. The electrical connection 110 can enable the electrodes to be supplied with electrical energy. In the illustrated configuration, the electrical connection 110 can be near the proximal end 116 of the hand tool 100.

Electrosurgical devices are useful for cauterization, hemostasis, and for tissue dissection. Electrosurgical devices most commonly involve radiofrequency (RF) energy wherein a voltage gradient is produced between two points and current flows through the tissue, dissipating energy as heat. This in turn allows refolding of protein and cauterization or dissection of tissue. The electrodes 192, 292 can be configured for cauterization, hemostasis, and tissue dissection. Other modes of electrical current transmission are contemplated.

The hand tool 100 can allow current to flow from the location where electrical energy is supplied to the electrodes 192, 292. The hand tool 100 can have a current passage that allows current to flow through the hand tool 100 and to the electrodes 192, 292. The hand tool 100 can be sufficiently insulated to prevent the dissipation of electrical energy. The hand tool 100 can be grounded. The hand tool 100 can be designed to operate in conjunction with current generators and other electrical devices. The majority of the hand tool can be excluded from electrical current. The current can be provided through a wire. The current can be provided through an inset. The current can be provided through multiple layering of dielectric-conductive-dielectric coatings.

Figure 12:
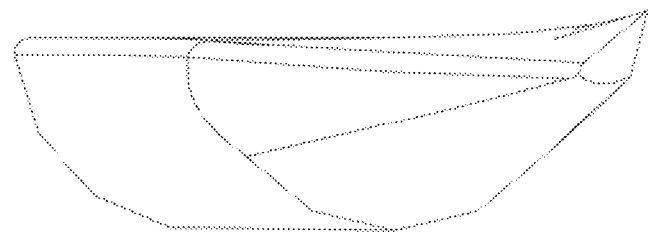
FIG. 12 is an embodiment of a blade.
Figure 13:
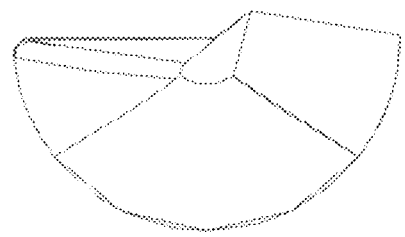
FIG. 13 is a view of the blade of FIG. 12.
Figure 14:
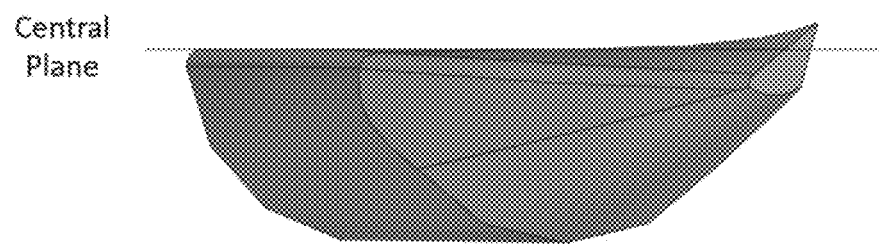
FIG. 14 is a view of the blade of FIG. 12.
Figure 15:
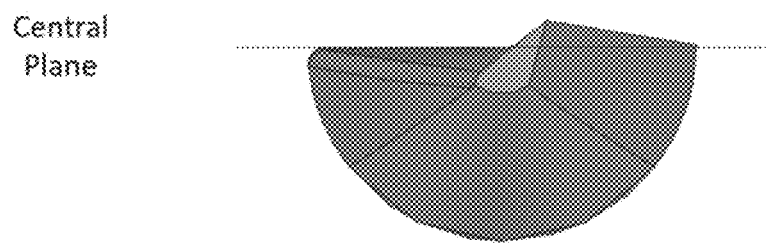
FIG. 15 is a view of the blade of FIG. 12.
Figure 16:
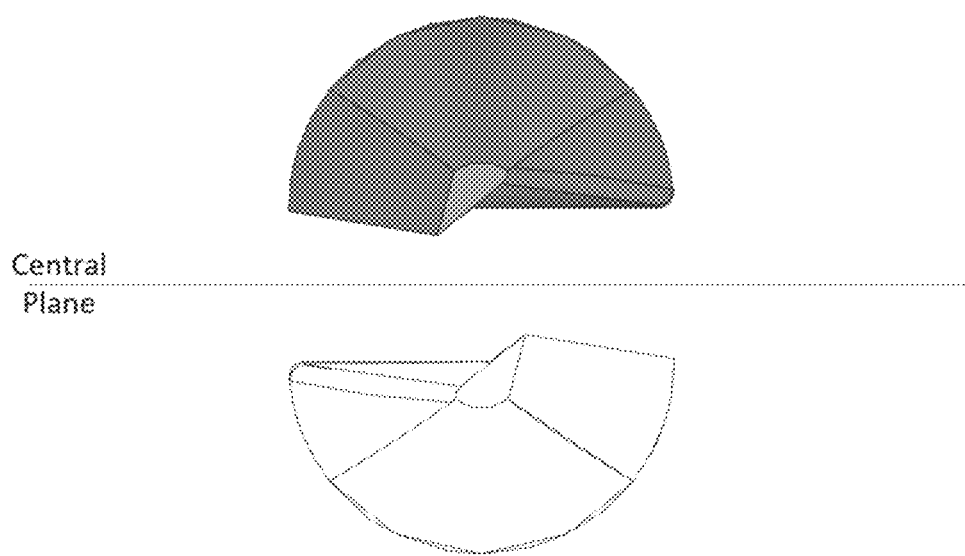
FIG. 16 is a view of a pair of blades.
Figure 17:
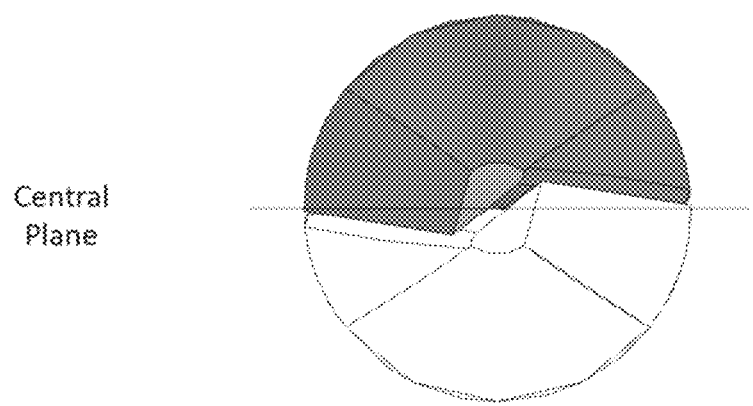
FIG. 17 is a view of a pair of blades.
Figure 18:
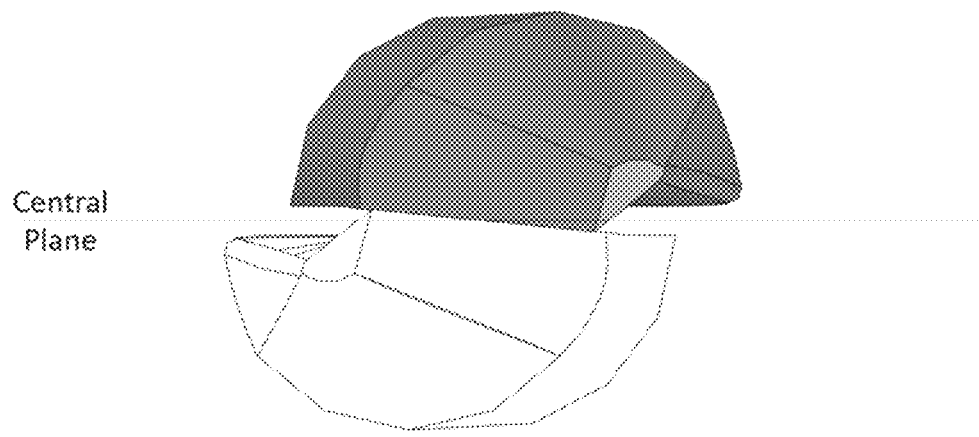
FIG. 18 is a view of a pair of blades.

FIG. 12 is an embodiment of a blade. The blade can be used with any surgical hand tool including those described in the appendix. FIGS. 13-15 are views of the blade of FIG. 12. FIGS. 16-18 are views of a pair of blades.

The blade can be used in electrosurgery. The blade can deliver energy varying in frequency, voltage, current, or duty cycle. The blades can transmit energy to tissue. The blades can be considered an end effect device. The blade can be capable of delivering multiple types of energy. The blade can be capable of delivering multiple forms of energy. The forms of energy can include mechanical, electrical, ultrasonic, etc. Unique and separate end effect devices are often required to deliver each of these energy types to achieve the desired tissue effect. End effect devices capable of performing multiple functions are advantageous.

The blade can have some portions or surfaces optimized to transfer electrical energy. The blade can have other portions or surfaces optimized to transfer mechanical energy, such as compression or shearing. The blade can have some or any portion of any surface optimized to transfer any portion of electrical or mechanical energy.

In some embodiments, two or more blades are utilized. The two blades can be identical. The two blades can be mirror images. The two blades can be symmetrical. The two blades can be similar.

The blades can be configured for shearing or scissoring. Shearing of tissue involves interference of blades at a focal point. Blade interference must be sufficient to shear the tissue and not allow it to pass, unaffected, between the blades. The blades can be configured to produce shearing action in addition to transferring other forms of energy. The blades can be configured to transition between various modes of operation without excessive stress to the user or device.

Scissor blades often rotate about an axis across a plane where each of the scissor blades crosses the plane, causing interference with the opposing blade. Scissor blades in surgical devices capable of delivery other forms of energy can have their collective rotation axis reestablished to allow other movements. Scissor blades in surgical devices capable of delivery other forms of energy can have their collective rotation axis reestablished to facilitate compression or delivery of electrosurgical energy. The rotation axis can be reestablished to allow the multi-tool to have both a shearing function and an energy delivery function. Along with the axis, interference between the blades must also be selectively reestablished.

In some embodiments, the rotation axis or scissor axis is established in only the shearing mode. The rotation axis can be reestablished by changing the axis angle of one blade relative to the blade of the other axis, while keeping some portion of the blades in proximity. In some embodiments, the rotation axis or scissor axis is removed entirely from the other blade. The axis can then be re-established then the blades are approximated. Interference between the blades can be minimized in the neutral position while the axis is re-established, minimizing forces needed to generate shearing blade interference.

In some embodiments, shearing blades that cross the plane while the two blades are aligned generate interference as the two scissor blades are opened or rotationally moved in opposing directions across the central plane. In some embodiments, shearing blades that cross the central plane while the blades are open can maintain interference for any given level or distance before relaxing near alignment. Each blade may have sufficient relief for the portions of the opposing blade crossing the central plane.

The end effect device can include two blades. The end effect device can be capable of delivering at least mechanical and electrical energy to tissue. The two blades directly deliver mechanical energy to tissue. The two blades shear or scissor the tissue. The two blades directly deliver electrical energy to tissue. The two blades can include electrodes to deliver energy. The one or more electrodes can be located on any surface or portion of one of the blades. The one or more electrodes can be located on any surface or portion of both of the blades. FIGS. 12-13 show the blade shape. FIGS. 14-18 show two blades and the central plane.

The blades can be formed such that movement toward and away from a central plane is selectively restricted.

The blades can be formed such that a portion of each of the components protrude to the other side of a central plane. FIG. 17 shows a portion of each blade protrudes to the other side of a central plane. A portion of each blade protrudes into the other blade. The blades can be formed such that moving the blades to the central plane allows selective restriction of movement away from the central plane.

The blades can be formed such that opposing movement along the same central plane produces interference between the two components. FIG. 18 shows that opposing movement along the central plane produces interference between the two components. FIG. 18 shows a shearing or scissoring motion.

The blades can be formed such that one or more surfaces are compatible with transmission of electrosurgical energy. The blades can be formed such that one or more surfaces are compatible with transmission of pinching mechanical energy. The blades can be formed such that one or more surfaces are compatible with transmission of shearing mechanical energy.

An electrosurgical system can include an electrosurgical generator and an adapter connected to the electrosurgical generator. The adapter is configured to selectively transmit one or more energy outputs from the electrosurgical generator to an end effect device. At least one of the electrosurgical generator and the adapter are configured to be controlled by one or more control device. An electrosurgical system can include a control device connected to an electrosurgical generator. The control device can be configured to selectively transmit control instructions to the electrosurgical generator. The control device can be configured to receive a control signal from a user. An electrosurgical apparatus can include a pair of blades configured to deliver at least mechanical and electrical energy to tissue. Each blade can include a portion configured to protrude to the other side of a central plane. An electrosurgical apparatus can include a first tip comprising a first tip central plane and a second tip comprising a second tip central plane, wherein the electrosurgical apparatus has a first configuration wherein the first and second tips operate as forceps, and wherein the electrosurgical apparatus has a second configuration wherein the first and second tips operate as scissors. The electrosurgical apparatus can have restricted movement in the forceps configuration and limited shearing movement in the scissors configuration.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above.

What is claimed is:

1. An electrosurgical system comprising:
   a single end-effect device configured to provide various energy effects that include (1) cut and coagulation functions through monopolar energy, (2) mechanical shearing, (3) mechanical energy, and (4) coagulation through bipolar energy;
   an electrosurgical generator comprising separate and distinct circuits and outputs to deliver various forms of energy;
   a control device;
   an adapter electrically positioned between the control device and the electrosurgical generator and configured to:
      receive one or more control inputs from the control device;
      determine a form of energy to provide to the single end-effect device based on the one or more control inputs from the control device to cause the single-end effect device to provide one or more of the various energy effects;
      communicate a control signal based on the one or more control inputs to the electrosurgical generator to cause the electrosurgical generator to deliver the form of energy;
      selectively transmit a first energy output to the single end-effect device responsive to a first energy output from the electrosurgical generator, the first energy output corresponding to a monopolar electrosurgery mode; and
      selectively transmit a second energy output to the single end-effect device responsive to a second energy output from the electrosurgical generator, the second energy output corresponding to a bipolar electrosurgery mode at a different time than the monopolar electrosurgery mode;
   wherein the single end-effect device includes a first tip comprising an electrode and a second tip comprising an electrode, wherein at least the electrode of the first tip is configured to be activated for the monopolar electrosurgery mode, wherein the electrodes of both the first tip and the second tip are configured to be activated for the bipolar electrosurgery mode, wherein the adapter is configured to activate either the monopolar electrosurgery mode or the bipolar electrosurgery mode through detection of a mechanical configuration of the single end-effect device.

2. The electrosurgical system of claim 1, wherein the adapter is configured to transmit different energy effects separately.

3. The electrosurgical system of claim 1, wherein the adapter is configured to transmit different energy effects sequentially.

4. The electrosurgical system of claim 1, wherein the single end-effect device comprises a configuration wherein the first and second tips operate as a monopolar electrode.

5. The electrosurgical system of claim 1, wherein the single end-effect device comprises a configuration wherein the first and second tips operate as bipolar forceps.

6. The electrosurgical system of claim 1, wherein the single end-effect device comprises a configuration wherein first and second tips operate as scissors.

7. The electrosurgical system of claim 1, wherein the single end-effect device is configured to have restricted movement in a forceps configuration and limited shearing movement in a scissors configuration.

8. The electrosurgical system of claim 1, wherein, when in the monopolar electrosurgery mode, the adapter is configured to prevent energy output associated with the monopolar electrosurgery mode being transmitted to another output circuit associated with the bipolar electrosurgery mode that is not being used.

9. The electrosurgical system of claim 1, wherein the monopolar electrosurgery mode and the bipolar electrosurgery mode deliver different voltage.

10. The electrosurgical system of claim 1, wherein the single end-effect device comprises a surgical hand tool configured to function as electrocoagulation bipolar forceps.

11. The electrosurgical system of claim 1, wherein the single end-effect device comprises a surgical hand tool configured for monopolar electrocoagulation, fulguration, monopolar detection, and monopolar stimulation.

12. The electrosurgical system of claim 1, wherein the adapter transmits one form of electrosurgical energy to an end effect device through a single or any number of combination of inputs.

13. The electrosurgical system of claim 1, wherein the adapter transmits one form of electrosurgical energy through a switch.

14. The electrosurgical system of claim 1, wherein the adapter transmits one form of electrosurgical energy through a sensor.

15. The electrosurgical system of claim 1, wherein the adapter transmits one form of electrosurgical energy through an algorithm.

16. The electrosurgical system of claim 1, wherein the first tip and the second tip are together to deliver energy.

17. The electrosurgical system of claim 1, wherein the electrosurgical system is configured to operate as monopolar electrocautery forceps or bipolar electrocautery forceps.

18. The electrosurgical system of claim 1, wherein the electrosurgical system is configured to operate as a two-bladed probe.

19. The electrosurgical system of claim 1, further comprising electrical leads to supply the electrodes with energy.

20. The electrosurgical system of claim 1, wherein the electrosurgical system is configured for cauterization, hemostasis, and tissue dissection.

21. The electrosurgical system of claim 1, wherein the first tip has a protrusion configured to engage with a recess of the second tip to prevent over travel between the first tip and the second tip when collapsed to a probe configuration.

* * * * *